(12) United States Patent
Marinkovic

(10) Patent No.: US 11,622,789 B2
(45) Date of Patent: Apr. 11, 2023

(54) SURGICAL SYSTEMS AND METHODS FOR CONTROLLING AN ANGULAR POSITION TRAJECTORY FOR TISSUE SHAVERS AND OTHER ROTATING SURGICAL INSTRUMENTS

(71) Applicant: COVIDIEN LP, Mansfield, MA (US)

(72) Inventor: Aleksandar Marinkovic, Brookline, MA (US)

(73) Assignee: Covidien LP, Mansfield, MA (US)

( * ) Notice: Subject to any disclaimer, the term of this patent is extended or adjusted under 35 U.S.C. 154(b) by 216 days.

(21) Appl. No.: 16/410,025

(22) Filed: May 13, 2019

(65) Prior Publication Data

US 2020/0360041 A1 Nov. 19, 2020

(51) Int. Cl.
| | | |
|---|---|---|
| A61B 17/3205 | (2006.01) | |
| A61B 17/32 | (2006.01) | |
| A61B 17/3207 | (2006.01) | |
| A61B 17/00 | (2006.01) | |

(52) U.S. Cl.
CPC .... *A61B 17/3205* (2013.01); *A61B 17/32002* (2013.01); *A61B 17/320783* (2013.01); *A61B 2017/00017* (2013.01); *A61B 2017/00132* (2013.01); *A61B 2017/00398* (2013.01); *A61B 2017/320024* (2013.01); *A61B 2017/320028* (2013.01); *A61B 2217/005* (2013.01)

(58) Field of Classification Search
CPC ........ A61B 17/3205; A61B 17/320783; A61B 17/32002; A61B 2017/320024; A61B 2017/320028; A61B 2017/00017; A61B 2017/00132
See application file for complete search history.

(56) References Cited

U.S. PATENT DOCUMENTS

| | | |
|---|---|---|
| 5,556,396 A | 9/1996 | Cohen et al. |
| 5,709,224 A | 1/1998 | Behl et al. |
| 6,485,486 B1 | 11/2002 | Trembly et al. |

(Continued)

FOREIGN PATENT DOCUMENTS

WO 2015023965 A1 2/2015

OTHER PUBLICATIONS

Extended European Search Report issued in corresponding European Application No. 20173821.8 dated Aug. 6, 2020, 9 pages.

(Continued)

*Primary Examiner* — Katherine M Shi
*Assistant Examiner* — Mohammed S Adam
(74) *Attorney, Agent, or Firm* — Carter, DeLuca & Farrell LLP

(57) ABSTRACT

A surgical instrument configured to cut tissue includes an outer member and an inner member at least partially received within the outer member. The outer member includes a cutting window near a distal end thereof. A driving assembly is coupled to the inner member and configured to cause the inner member to rotate around and move along a longitudinal axis of the outer member. A controller is configured to control the driving assembly to control at least one of an angular position, an angular velocity, or an angular acceleration of the inner member according a plurality of piecewise continuous profiles. The initial and final angular velocities of the inner member are zero, and the inner member cuts tissue extending into the cutting window.

17 Claims, 14 Drawing Sheets

(56) References Cited

U.S. PATENT DOCUMENTS

| | | | |
|---|---|---|---|
| 6,896,682 B1 | 5/2005 | McClellan et al. | |
| 8,591,464 B2 | 11/2013 | Kumar et al. | |
| 9,084,847 B2 | 7/2015 | Klein et al. | |
| 2008/0262476 A1* | 10/2008 | Krause | A61B 17/32002 604/540 |
| 2014/0324065 A1 | 10/2014 | Bek et al. | |
| 2015/0327919 A1* | 11/2015 | Clopp | A61B 17/22 606/41 |
| 2016/0206339 A1* | 7/2016 | Akilian | A61B 17/32002 |
| 2017/0055810 A1 | 3/2017 | Germain et al. | |
| 2017/0210064 A1 | 7/2017 | Aw et al. | |
| 2017/0258512 A1* | 9/2017 | Germain | A61B 17/1626 |
| 2018/0360470 A1* | 12/2018 | Parfett | A61B 34/76 |
| 2018/0364137 A1* | 12/2018 | Mark | A01N 1/0252 |
| 2019/0059983 A1 | 2/2019 | Germain et al. | |

OTHER PUBLICATIONS

European Communication for application No. 20 173 821.8 dated Jun. 22, 2022.

* cited by examiner

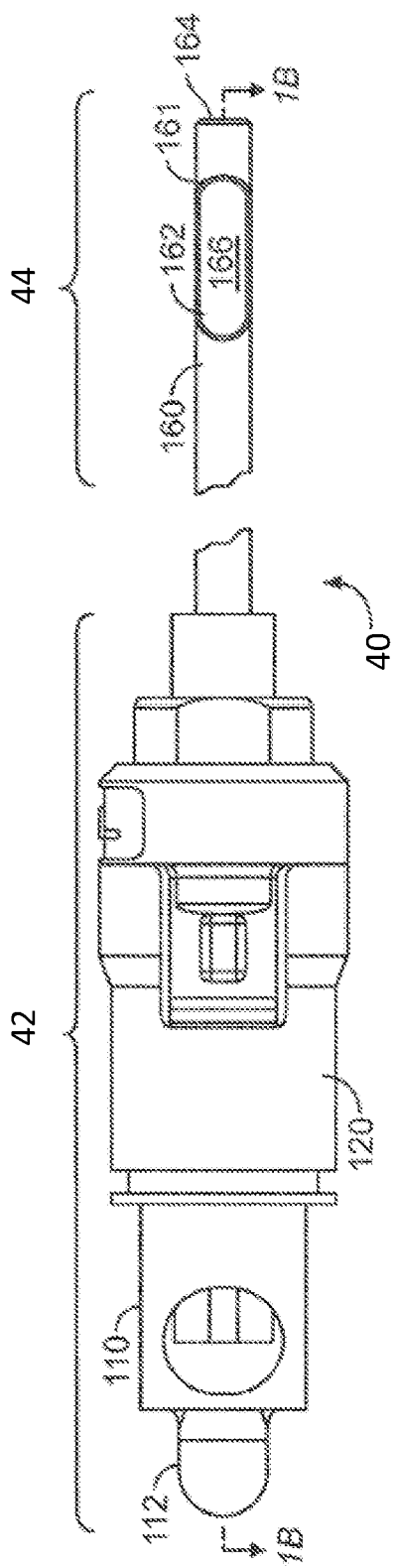
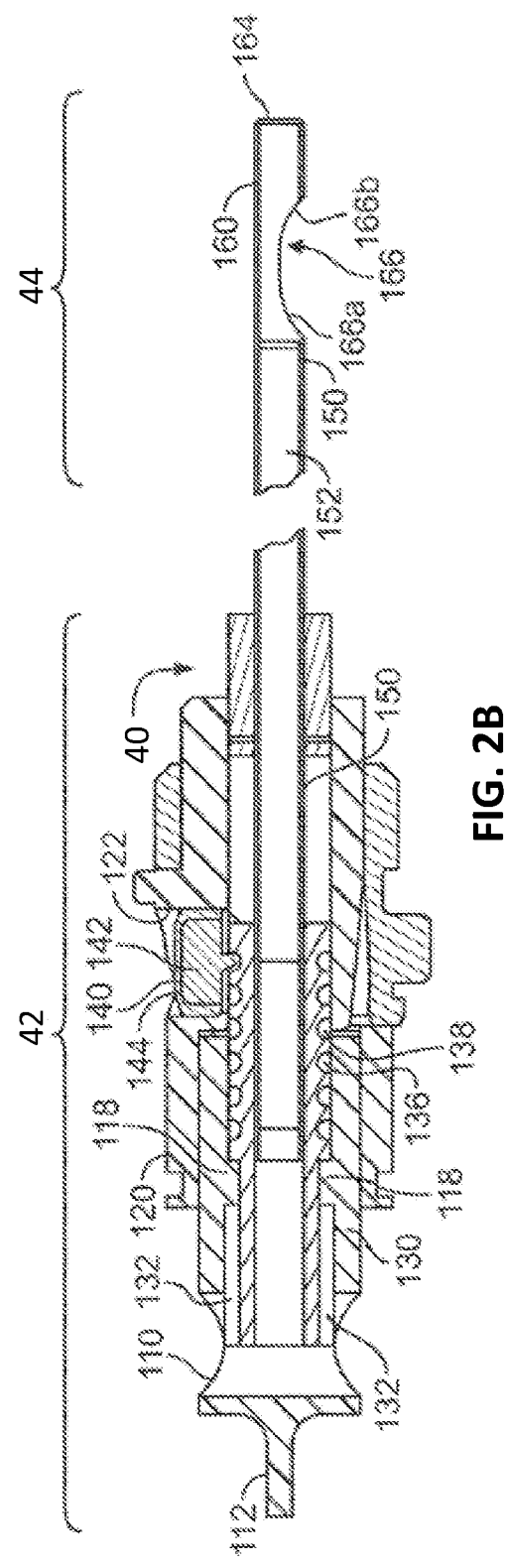
FIG. 2A
FIG. 2B

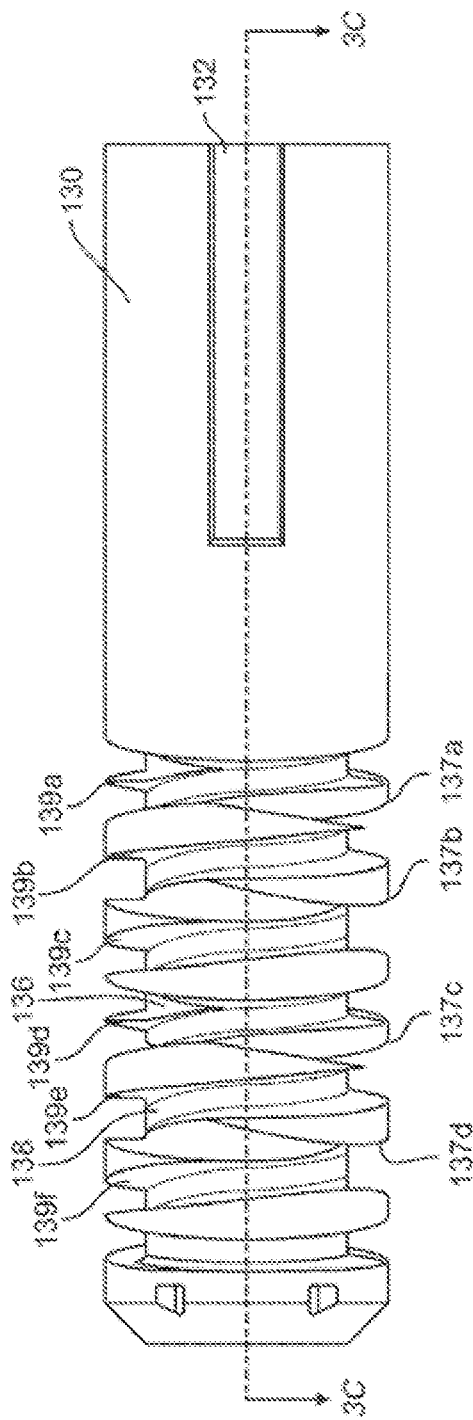
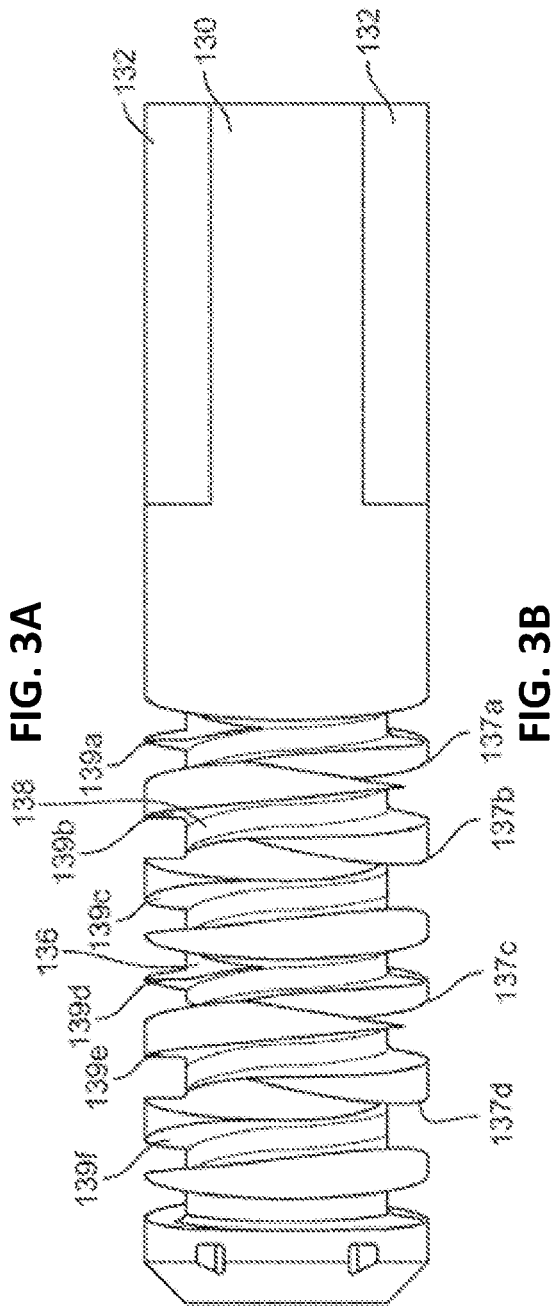
FIG. 3A
FIG. 3B

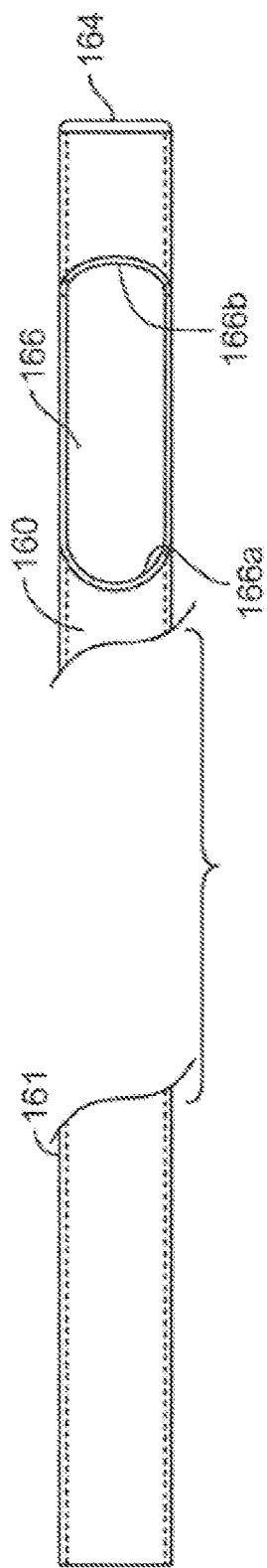
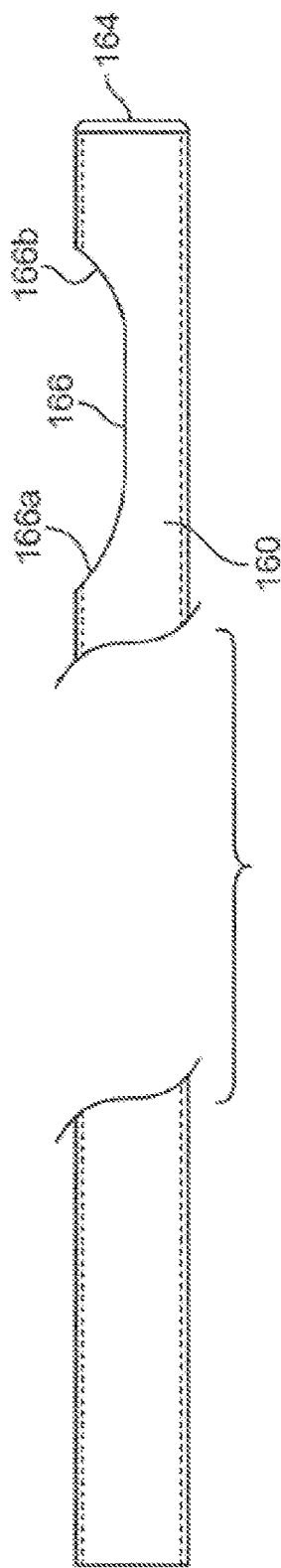
FIG. 5A
FIG. 5B

SURGICAL SYSTEMS AND METHODS FOR CONTROLLING AN ANGULAR POSITION TRAJECTORY FOR TISSUE SHAVERS AND OTHER ROTATING SURGICAL INSTRUMENTS

FIELD

The present disclosure is generally related to surgical instruments, and more particularly, to surgical systems and methods for controlling an angular position for tissue shavers and other rotating surgical instruments.

BACKGROUND

Surgical instruments that cut tissue, such as tissue shavers, generally include an outer tube and an inner member that rotates and/or translates axially within the outer tube. The outer tube and inner member may interact to create shear forces that cut tissue.

SUMMARY

This disclosure generally relates to surgical systems and methods for controlling an angular position for tissue shavers and other rotating surgical instruments based on piecewise continuous profiles. By following or mimicking the piecewise continuous profiles, the tissue shaver is able to cut and aspire tissue in a desired way.

Surgical instruments in accordance with aspects of the present disclosure are configured to cut tissue and include an outer member and an inner member at least partially received within the outer member. The outer member includes a cutting window near a distal end thereof. A driving assembly is coupled to the inner member and configured to cause the inner member to rotate around and move along a longitudinal axis of the outer member. A controller is configured to control the driving assembly to control at least one of an angular position, an angular velocity, or an angular acceleration of the inner member according a plurality of piecewise continuous profiles. The initial and final angular velocities of the inner member are zero, and the inner member cuts tissue extending into the cutting window.

In an aspect of the present disclosure, a forward velocity of the inner member is higher than a backward velocity of the inner member.

In another aspect of the present disclosure, the inner member moves from a proximal-most position to a distal-most position for a predetermined period. The inner member moves from the distal-most position to the proximal-most position for the predetermined period. The inner member switches a movement direction every predetermined period.

In another aspect of the present disclosure, a first profile includes a continuous function for the angular position, the angular velocity, or the angular acceleration for the inner member during a rise time. A second profile, which follows the first profile, includes a constant velocity of the inner member after the rise time. A third profile, which follows the second profile, includes a continuous function for the angular position, the angular velocity, or the angular acceleration for the inner member after the second profile.

In still another aspect of the present disclosure, the inner member is fixed to a drive component that includes a first helical groove and a second helical groove thereon along the longitudinal axis. The inner member linearly moves along the longitudinal axis based on the first and second helical grooves while the inner member rotates.

In yet another aspect of the present disclosure, the surgical instrument further includes an encoder configured to count a number for the angular position.

In still yet another aspect of the present disclosure, the inner member includes a first helical groove and a second helical groove thereon along the longitudinal axis. The inner member linearly moves along the longitudinal axis based on the first and second helical grooves while the inner member rotates.

A method for cutting tissue provided in accordance with aspects of the present disclosure includes inserting a distal portion of a tissue shaver inside of a subject adjacent tissue to be cut and removed, supplying power to a motor to drive the tissue shaver, and controlling the supply of power to the motor to thereby control rotation and reciprocation of an inner member of the tissue shaver according to a plurality of piecewise continuous profiles so that the inner member rotates and reciprocates back and forth inside of an outer member of the tissue shaver. The initial and final velocities of the inner member are zero.

In an aspect of the present disclosure, the method further includes cutting tissue engaged with a cutting window of the outer member when the inner member moves forward to a distal-most position. The method also includes aspirating the cut tissue when the inner member moves back from a distal-most position of the outer member.

In another aspect of the present disclosure, controlling the rotation of the inner member includes following a first profile so that the inner member achieves a constant velocity from the initial velocity during a rise time. The first profile is a continuous function for an angular position of the inner member.

In still another aspect of the present disclosure, controlling the rotation of the inner member further includes following a second profile after the first profile so that the inner member maintains the constant velocity. Further, controlling the rotation of the inner member includes following a third profile after the second profile so that the inner member achieves the final velocity from the constant velocity.

In yet another aspect of the present disclosure, the method further includes changing a movement direction of the elongated inner member every predetermined period. The movement direction is changed based on a first helical groove and a second helical groove on an outer surface of the elongated inner member.

In still yet another aspect of the present disclosure, the movement direction is changed based on a first helical groove and a second helical groove on a drive component engaged with the inner member.

A non-transitory computer readable storage medium provided in accordance with aspects of the present disclosure includes computer-executable instructions that, when executed by a computer, perform a method for shaving tissue. The method includes inserting a distal portion of a tissue shaver inside of a subject adjacent tissue to be cut and removed, supplying power to a motor to drive the tissue shaver, and controlling the supply of power to the motor to thereby control rotation and reciprocation of an inner member of the tissue shaver according to a plurality of piecewise continuous profiles so that the inner member rotates and reciprocates back and forth inside of an outer member of the tissue shaver. The initial and final velocities of the inner member are zero.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Various embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

FIG. 2A is a partial top view of the tissue shaver of the system of FIG. 1;

FIG. 2B is a cross-sectional view taken along section line 1B-1B in FIG. 2A;

FIG. 3A is a top view of a helical member of the tissue shaver of FIG. 2A;

FIG. 3B is a side view of the helical member of FIG. 3A;

FIG. 5A is a partial top view of an outer member of the tissue shaver of FIG. 2A;

FIG. 5B is a partial side view of the outer member of FIG. 5A;

DETAILED DESCRIPTION

Tissue shavers cut tissues for medical purposes, such as tissue removal, diagnosis, prognosis, or other surgeries. A tissue shaver may include an outer tube and an inner member, where the inner member moves relative to the outer tube to create shear forces that are employed to cut tissue. According to various aspects of this disclosure, embodiments of tissue shavers achieve desired relative movements between the outer tube and the inner member based on piecewise continuous profiles. According to various aspects of the present disclosure, the inner member moves at different rates depending on its angular position and/or direction of movement relative to the outer tube based on piecewise continuous profiles, which provide reference angular positions, velocities, accelerations, and/or jerks of the movement of the inner member. Thus, the tissue shavers provide smooth motions that increase their cutting performance and/or other aspects of operation thereof.

The terms "continuous" and "smooth" used in this disclosure mean there is no disjoint, no abrupt jump, and no hall at any point in a single curve along the time axis. That is, the curve can be drawn with a pencil without being lifted off from a paper. Mathematically speaking, left and right limits around each point in time have a value, and the left and right limits are equal to the assigned value at that point. Thus, the piecewise continuous profiles may provide no overshoots in operations of the tissue shaver. In other words, the operation of the tissue shaver is smooth, controllable, and predictable, thus, increasing effectiveness of the operations.

The term "angular position" means a position around a center in angle, i.e., radian or degree ("°"). The term "angular velocity" or just "velocity" means a first derivative of the angular position. Further, the velocity as used in this disclosure has a magnitude and a direction. In contrast, when a speed is used, the speed is a scalar, meaning that it has a magnitude but not a direction. The term "angular acceleration" or just "acceleration" means a second derivative of the angular position or a first derivative of the angular velocity. The term "angular jerk" or just "jerk" means a third derivative of the angular position, a second derivative of the angular velocity, or a first derivative of the angular acceleration.

Figure 1:
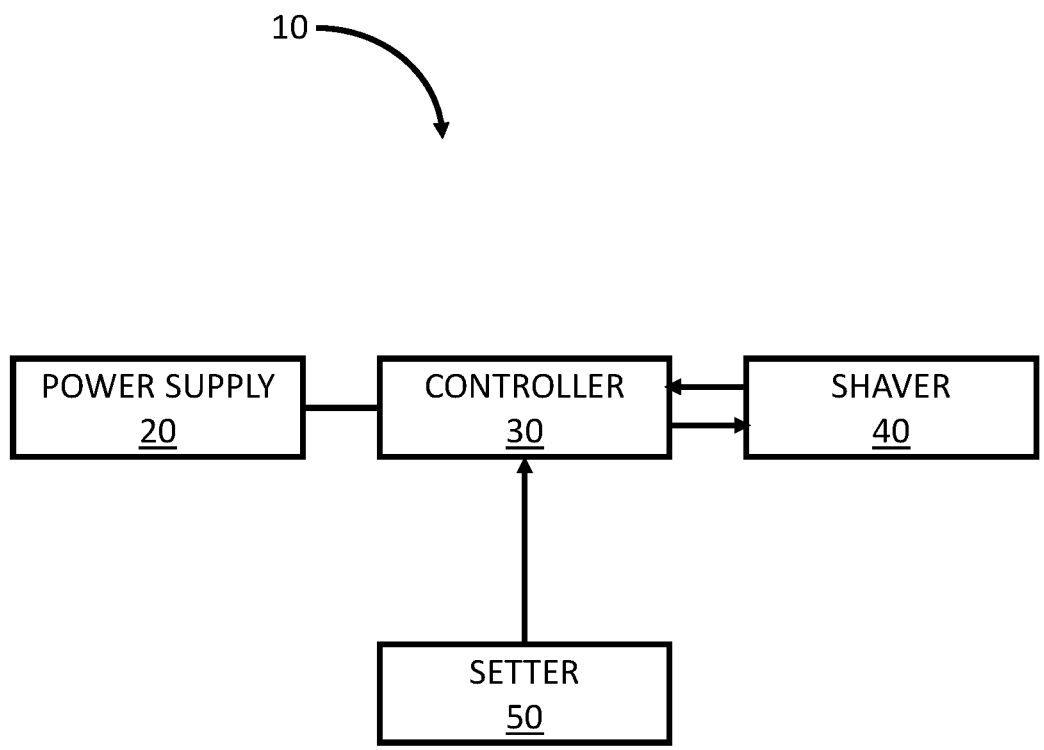
FIG. 1 is a block diagram that illustrates a surgical system for controlling an angular position, velocity, acceleration, or jerk for a tissue shaver in accordance with aspects of the present disclosure.

FIG. 1 illustrates a surgical system 10 for cutting tissue according to embodiments of the present disclosure. The surgical system 10 may include a power supply 20, a controller 30, a tissue shaver 40, and a setter 50. The power supply 20 may be a battery, a console, or an electrical outlet and is configured to power the controller 30, in particular, to drive the motor thereof.

The controller 30 includes a motor configured to drive the tissue shaver 40 and a control unit including a processor and memory, e.g., non-transitory computer-readable storage medium, storing instructions to be carried out by the processor to control performance of the tissue shaver 40. In an aspect, the processor of the controller 30 may control angular positions, velocities, accelerations, and/or jerks of the tissue shaver 40 by controlling the output of the motor which, in turn, may be accomplished by controlling the power delivered from power supply 20 to the motor of controller 30. In response, the tissue shaver 40 may provide feedback signals to the controller 30. Further, the setter 50 may provide reference angular positions, velocities, accelerations, and/or jerks for the tissue shaver 40 to the controller 30 independent or in conjunction with of the feedback signals. The controller 30 may compare the reference angular trajectories with the current angular trajectory based on the feedback signal and control the power supplied to the motor or otherwise control the motor so as to follow the reference angular trajectories for the tissue shaver 40.

The setter 50 may store piecewise continuous profiles to provide reference angular positions, velocities, accelerations, and/or jerks to the controller 30 for more than one disjoint period, when combined to form a full period, during which the tissue shaver 40 may make a unit back-and-forth movement. Each piecewise profile may include a continuous function for its corresponding disjoint period. When each profile is positioned or drawn in a corresponding disjoint period and combined with other profiles, the whole profile for the full period may form a continuous curve for angular position, velocity, and acceleration of the tissue shaver 40. In an aspect, the curve for the angular jerk for the full period may not be continuous.

Details of the tissue shaver 40 are described with reference to FIGS. 2A-8. However, it is contemplated that any other suitable tissue shaver or other rotating surgical instrument may be utilized in accordance with the present disclosure in place of tissue shaver 40. As shown in FIGS. 2A and 2B, the tissue shaver 40 may include a driving end portion 42 and a cutting end portion 44. The driving end portion 42 is located towards the proximal end of the tissue shaver 40 and the cutting end portion 44 is located towards the distal end of the tissue shaver 40.

An inner drive hub 110 and an outer hub 120 are disposed at the driving end portion 42. The inner drive hub 110 includes a drive coupler 112, which operably couples with the controller 30. The controller 30 turns the drive coupler 112 causing a helical drive member 130 and the inner drive hub 110 to rotate. The helical drive member 130 is located within the inner drive hub 110 and the outer hub 120. The helical drive member 130 and a coupling piece 140 engage each other, e.g., the coupling piece 140 is configured to ride within helical channels 136 and 138 of the helical drive member 130, so that rotation imparted to the helical drive member 130 by the drive coupler 112 also causes linear motion of the helical drive member 130 along the longitudinal axis of the helical drive member 130.

The tissue shaver 40 further includes an inner cutting member 150 and an outer member 160, as shown in FIG. 2B. The inner cutting member 150 may be tubular with a hollow interior 152 and used to cut or slice/shear tissue. The inner cutting member 150 is mechanically coupled, e.g., fixed, to the helical drive member 130 to enable linear and rotary motions of the inner cutting member 150 in conjunction with the linear and rotary motion of the helical drive member 130.

The outer member 160 may be also tubular with a hollow interior 162. The inner cutting member 150 is received inside the outer member 160. The outer member 160 is coupled to the outer hub 120. The outer member 160 may include a tip 164, which is blunt, e.g., the corners are rounded, or may define any other suitable configuration. At the cutting end portion 44 of the tissue shaver 40, the outer member 160 defines a cutting window 166 through a wall 161 (FIG. 2A) of the outer member 160, spaced-apart from the distal-most end of the outer member 160.

The inner drive hub 110 includes the drive coupler 112, a lumen 114, an aspiration opening 116, and at least one key 118. Debris at the cutting end portion 44 of the tissue shaver 40 may be aspirated through the inner cutting member 150 and the aspiration opening 116. The drive coupler 112 extends from a proximal end portion of the inner drive hub 110 and couples the inner drive hub 110 to the controller 30. The controller 30 may include a drive motor (not explicitly shown), powered by the power supply 20 (FIG. 1), that is coupled to the drive coupler 112 to cause the inner drive hub 110 to rotate. The inner drive hub 110 transfers the rotary motion imparted thereto to the helical drive member 130 while allowing the helical drive member 130 and the inner cutting member 150 (which is coupled to the helical drive member 130) to move axially along the axis of rotation and relative to the inner drive hub 110.

The at least one key 118 extends from a wall 111 of the inner drive hub 110. Each key 118 functions as a guide along one side of the inner drive hub 110. Each key 118 of the inner drive hub 110 engages a respective slot 132 of the helical drive member 130 so that rotation of the inner drive hub 110 causes the helical drive member 130 to rotate while allowing the helical drive member 130 to move linearly relative to the inner drive hub 110, e.g., each key 118 slides linearly along the respective slot 132. As shown in FIG. 2B, the at least one key 118 is shaped like a fin and the at least one slot 132 is located at the proximal end of the helical drive member 130 to receive the at least one key 118 of the inner drive hub 110. In alternative implementations, the at least one slot is conversely disposed in the wall 111 of the inner drive hub 110 while the at least one key extends from a wall of the helical drive member 130 to engage the at least one slot. In the illustrated implementations, a pair of keys 118 engages respective slots 132. In general, however, any number of keys 118 may extend from inner drive hub 110 to engage respective slots 132 in the wall of the helical drive member 130, or vice versa. In an aspect, the controller 30 may be coupled to the helical drive member 130 by gears or a gear and a spline gear.

Figure 3C:
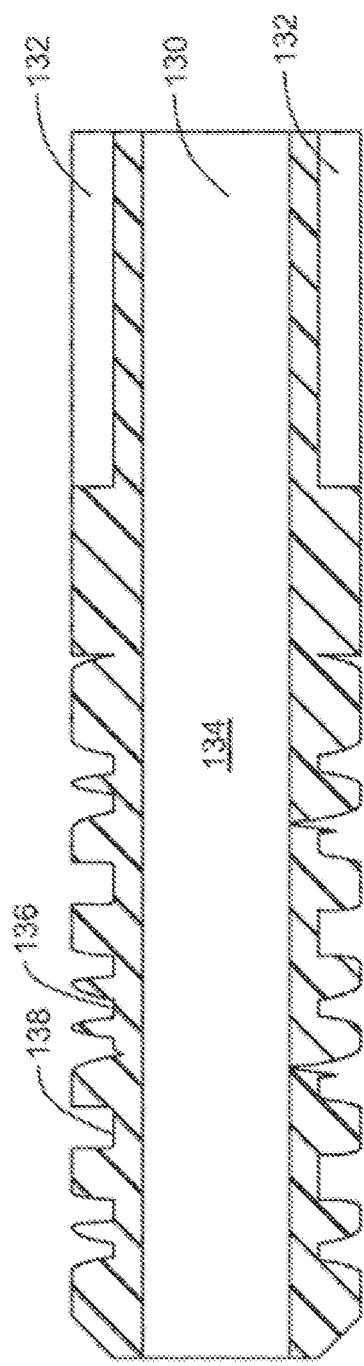
FIG. 3C is a cross-sectional view taken along section line 3C-3C of the helical member of FIG. 3A.
Figure 3D:
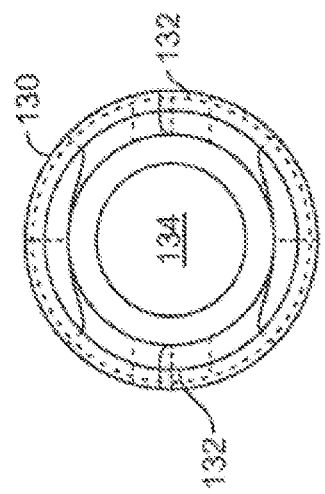
FIG. 3D is a proximal end view of the helical member of FIG. 3A.

The helical drive member 130 of the tissue shaver 40 is formed in a tubular shape with a lumen 134 extending therethrough, as shown in FIGS. 3C and 3D. The inner cutting member 150 may be disposed within the lumen 134 of the helical drive member 130 and fixed therein, for example, by set screws, epoxy, injection-molded, or overmolded plastic. In alternative implementations, the inner cutting member 150 may be coupled to the helical drive member 130 by a spline, gears, a gear and a spline, or in any other suitable manner.

The outer hub 120 of the tissue shaver 40 is formed of hard plastic and does not move. A cutout 122 is disposed within a wall of the outer hub 120, for example, centrally and aligned with the helical drive member 130. As shown in FIG. 2B, the coupling piece 140 is located in the cutout 122 of the outer hub 120.

As shown in FIG. 2B, the outer member 160 is disposed within the outer hub 120 and fixed therein by a coupling using, for example, set screws, epoxy, glue, insert molding, spin-welding, or in any other suitable manner.

Referring particularly to FIGS. 3A-3C, the helical drive member 130 also includes two helical channels 136 and 138. The helical channels 136 and 138 are disposed on a distal portion of the exterior surface of the helical drive member 130. As shown, the first helical channel 136 is right-hand threaded and the second helical channel 138 is left-hand threaded. The length of the distal portion of the helical drive member 130 with helical channels 136 and 138 may be longer, shorter, or equal to the length of the cutting window 166 (FIGS. 2A and 2B). The helical channels 136 and 138 may be smoothly blended together at their ends to form a continuous groove so that there is a smooth transition from one helical channel 136 to the other helical channel 138 at each end of the distal portion of the helical drive member 130. The continuous groove provides for linear motion of the inner cutting member 150 that includes moving distally over a length of travel and then changing direction and moving proximally over a length of travel and then changing direction to begin moving distally again. The length of travel may be determined as a function of the extent of the helical channels 136 and 138 over the helical drive member 130. The velocity of the linear motion may be determined as a function of the angle or pitch of the helical channels 136 and 138 and the rotational speed of the helical drive member 130. Changing the moving direction includes, while moving in a first direction, decelerating to zero velocity and then accelerating in the opposite direction.

In accordance with some implementations of the present disclosure, the helical drive member 130 may be mechanically driven by the motor of the controller 30 to move linearly over a length of travel and then change direction as a result of the interaction of the coupling piece 140 with the helical channels 136 and 138 and their blended ends. In such implementations, only a rotational force in a single rotational direction applied by the controller 30 to the helical drive member 130 is needed to drive the helical drive member 130 in a reciprocating manner That is, by driving the helical drive member 130, the helical drive member 130 is caused to rotate and move linearly in a back-and-forth motion. In an aspect, as helical drive member 130 is driven by the motor of the controller 30, the coupling piece 140 moves linearly over a length of travel and then changes direction as a result of the interaction of the coupling piece 140 with the helical channels 136 and 138 and the blended ends thereof. As a result, the inner cutting member 150 is caused to move linearly and then change direction when the inner cutting member 150 reaches its distal-most or proximal-most position.

Figure 4A:
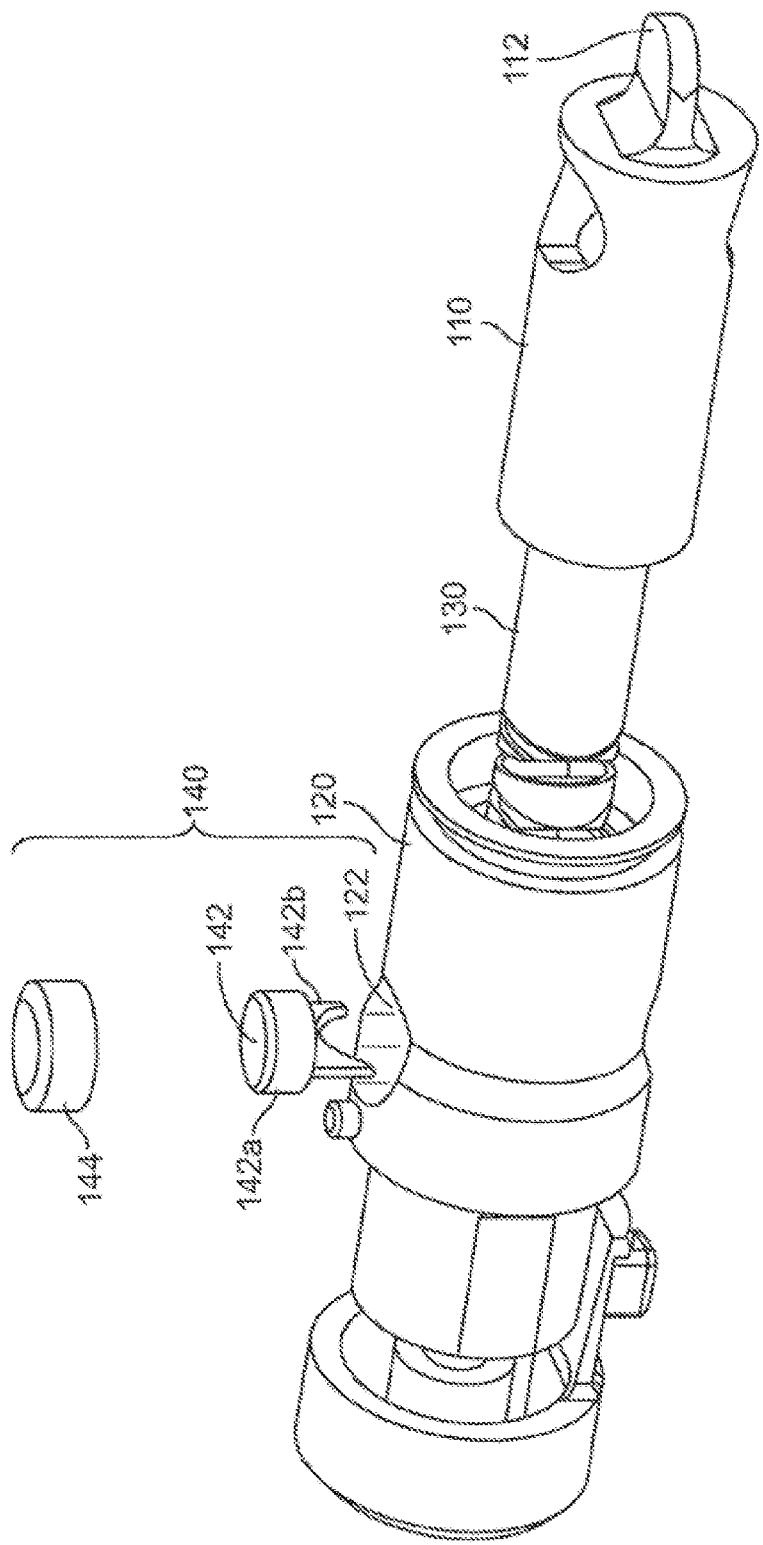
FIG. 4A is an exploded perspective view of a coupling piece and the helical member of the tissue shaver of FIG. 2A.
Figure 4B:
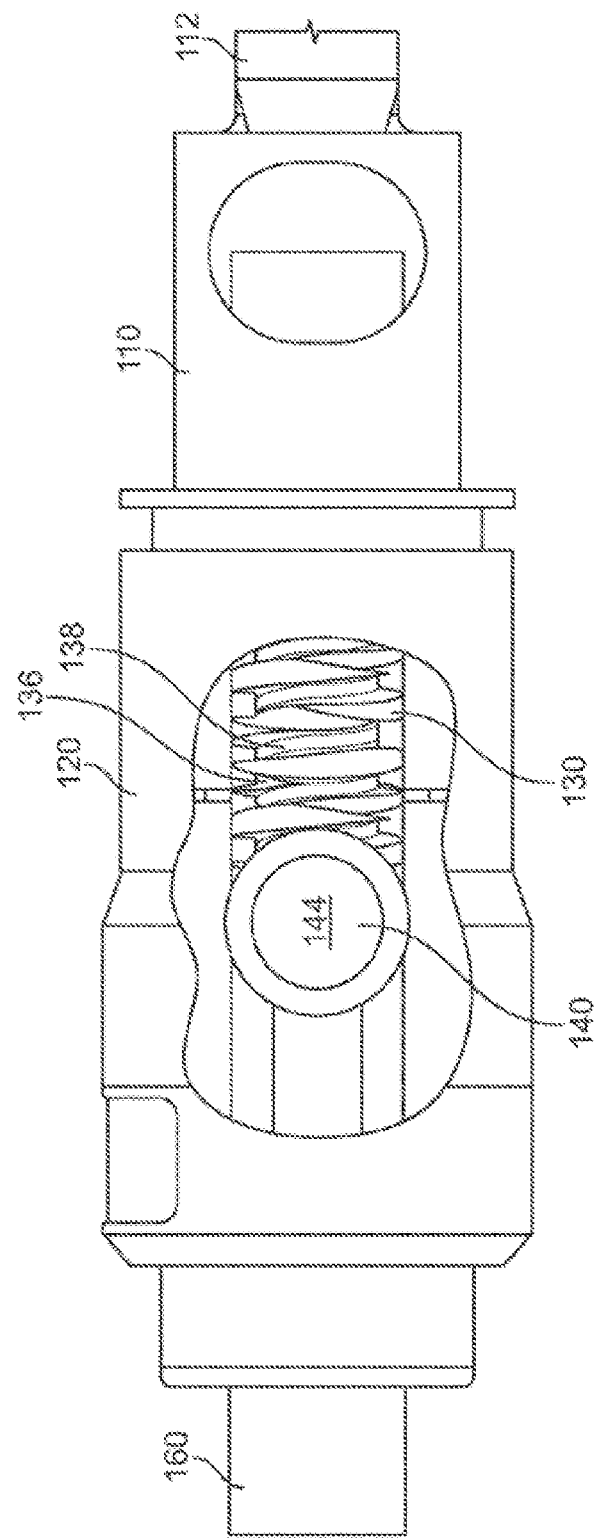
FIG. 4B is an assembled partial cutaway view of the coupling piece and the helical member shown in FIG. 4A.
Figure 4C:
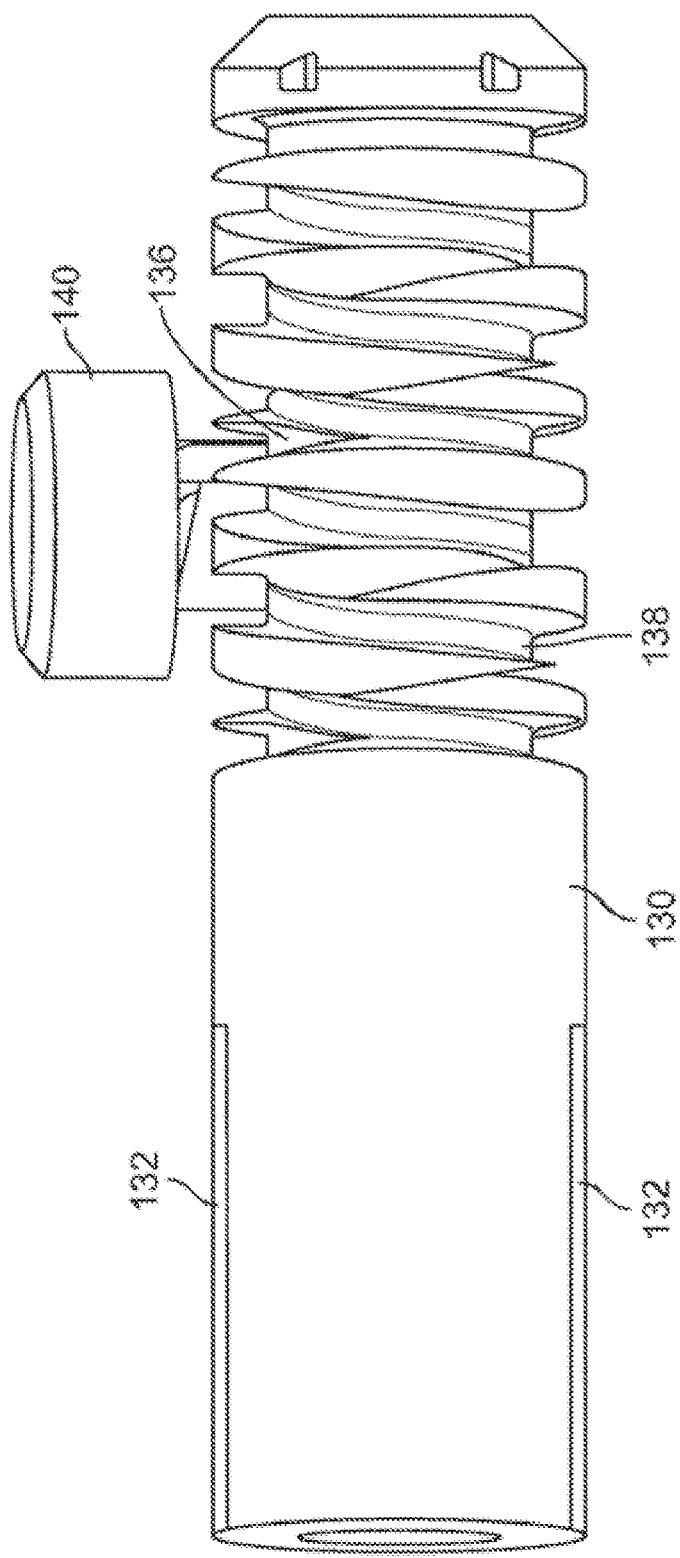
FIG. 4C is an assembled side view of the coupling piece and the helical member shown in FIG. 4A.
Figure 4D:
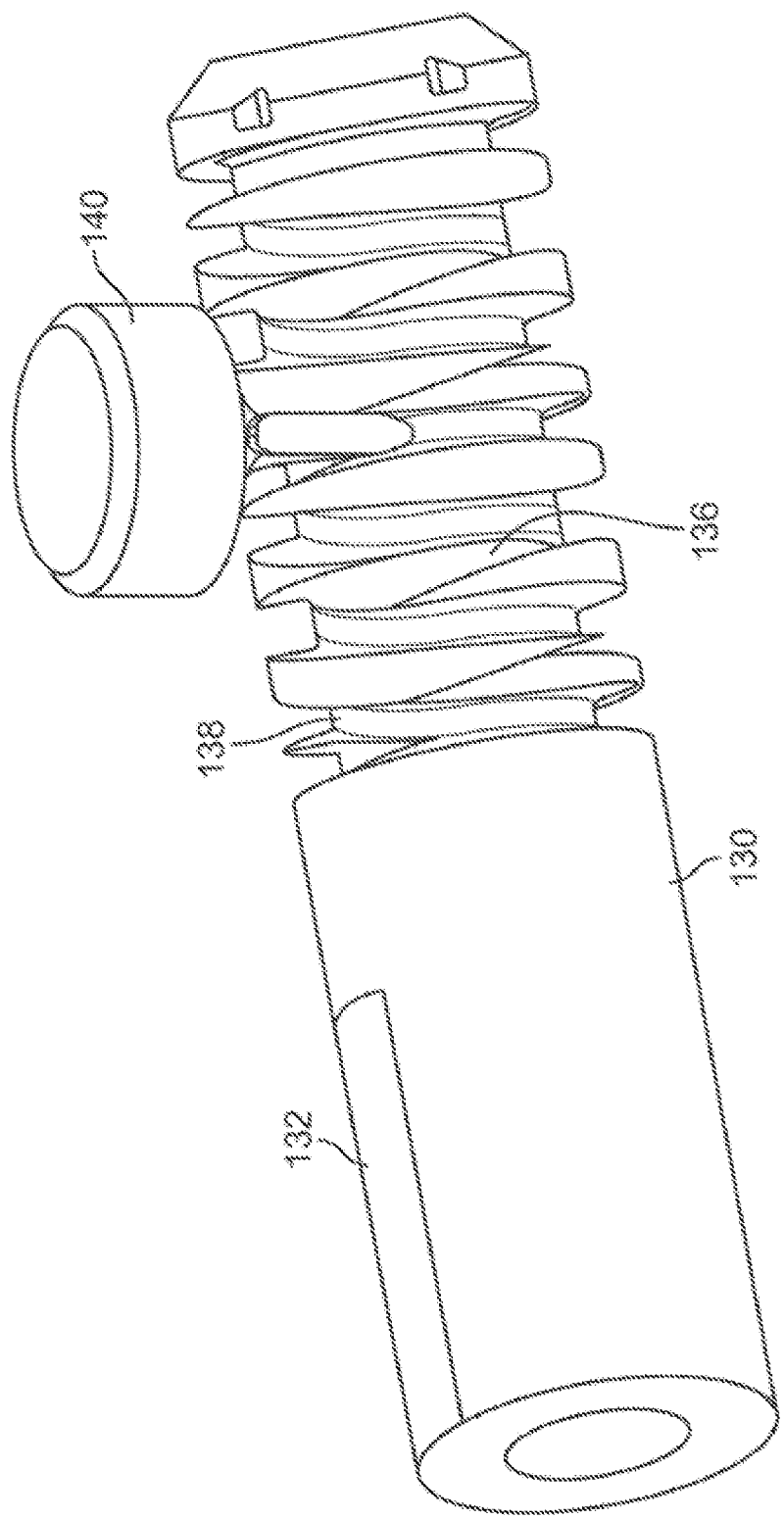
FIG. 4D is an assembled perspective view of coupling piece and the helical member shown in FIG. 4C.

Referring to FIG. 4A, the coupling piece 140 includes a follower 142 and a cap 144. Having the two helical channels 136 and 138 that are smoothly blended together at their ends to form a continuous groove in conjunction with the slot 132/key 118 coupling of the inner drive hub 110 and the helical drive member 130, the motor of the controller 30 only needs to rotate in a single direction and does not require reversal of the rotational direction upon the coupling piece 140 reaching the end of one of the helical channels 136 and 138. That is, the helical drive member 130 is caused to move distally in a first direction and then proximally in a second opposite direction without having to change the rotational direction of the helical drive member 130.

The follower 142 includes a cylindrical head 142a and two legs 142b. As shown in FIGS. 5B-5D, the legs 142b form an arch and rest in the channels of the helical channels 136 and 138 formed in the distal portion of the exterior surface of the helical drive member 130. The arch of the legs 142b is dimensionally related to the diameter described by the helical channels 136 and 138 of the helical drive member 130.

The cap 144 of the coupling piece 140, as shown in the partially exploded view of FIG. 4A, covers the follower 142 to provide a seal to allow sufficient suction to remove aspirated debris. Also, the cap 144 may be a separate piece from the follower 142 in order to allow the follower 142 to swivel.

As shown in FIGS. 5A and 5B, the cutting window 166 has a generally oblong shape and is disposed proximate to the tip 164 of the outer member 160 and along the length of the outer member 160 from the tip 164 to a position proximate the helical drive member 130. The cutting window 166 exposes the inner cutting member 150 over a length. The proximal end 166a of the cutting window 166 is U-shaped. The distal end 166b of the cutting window 166 is also U-shaped. It is understood, however, that the cutting window 166 may be shaped and/or positioned in a manner different from the illustrated embodiments. In some embodiments, the distal end 166b may optionally provide a sharp edge. In further embodiments, the distal end 166b may optionally have a saddle shape that forms a hook, which may pierce the targeted tissue to hold the tissue as the inner cutting member 150 cuts.

Figure 6:
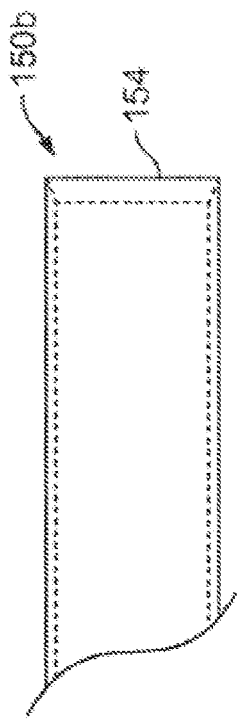
FIG. 6 is a partial side view of an inner member of the tissue shaver of FIG. 2A.
Figure 6:
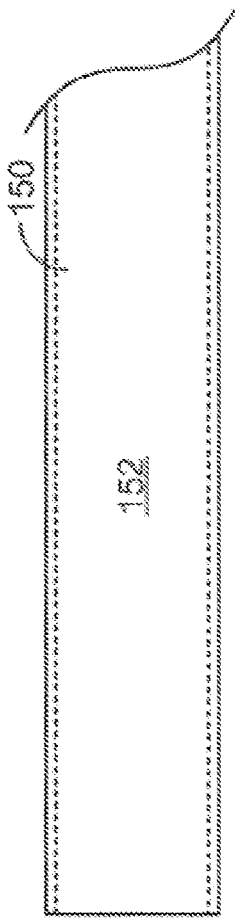

FIG. 6 shows that the inner cutting member 150 is generally tubular with a hollow interior 152. Aspiration of debris occurs through the hollow interior 152 of the inner cutting member 150, and through the lumen 134 (FIGS. 3C and 3D) of the helical drive member 130 to the aspiration opening 116 (FIG. 2A) of the inner drive hub 110. The distal end 150b of the inner cutting member 150 may be chamfered to a cutting edge 154 for cutting. The inner cutting member 150 simultaneously rotates about its axis and moves linearly along its axis of rotation to cut tissue. The cutting surface of the distal end 150b of the inner cutting member 150 shears tissue. For example, referring to FIG. 8, the tissue shaver 40 is placed tangentially against the targeted tissue such that the cutting window 166 exposes the inner cutting member 150 to the tissue. The tissue protrudes through the cutting window 166, e.g., via suction established through inner cutting member 150, prior to being cut by the inner cutting member 150. As the inner cutting member 150 rotates and moves linearly (e.g., downward in the orientation shown in FIG. 8), as shown by the arrows, the cutting edge 154 of the inner cutting member 150 shears the tissue as the inner cutting member 150 advances to cut the tissue. The cut is completed as the cutting edge 154 (FIG. 6) of the inner cutting member 150 advances beyond the distal end 166b (FIGS. 5A and 5B) of the cutting window 166 within the outer member 160.

Figure 7:
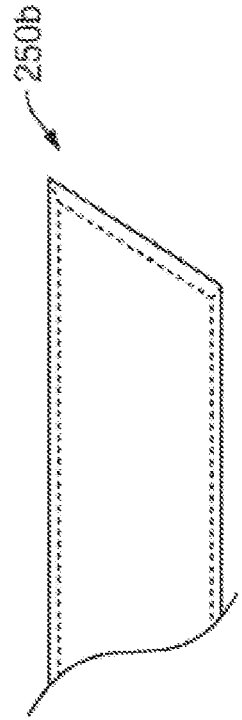
FIG. 7 is a partial side view of an alternate implementation of an inner member of the tissue shaver of FIG. 2A.
Figure 7:
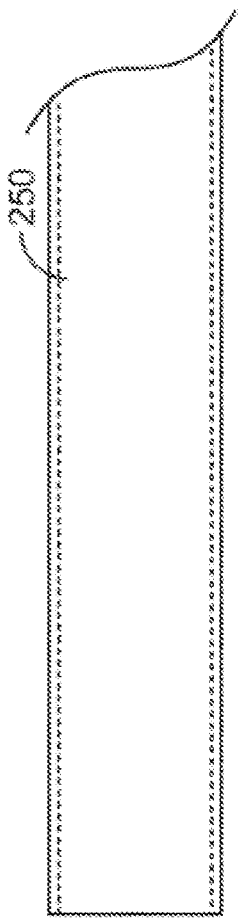
Figure 8:
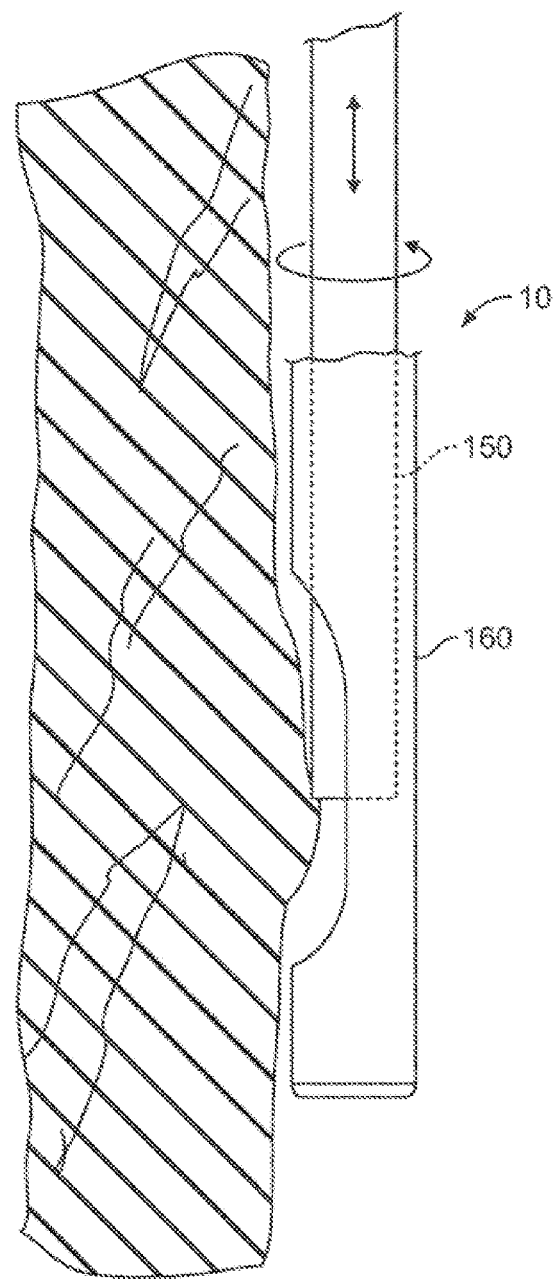
FIG. 8 illustrates a distal portion of the tissue shaver of FIG. 2A in use cutting tissue.

FIG. 7 shows an alternative embodiment of an inner cutting member 250. The distal end 250b of the inner cutting member 250 may be angled to a chamfered point so that the cut in the targeted tissue is initiated on one side and then extends across the width of the tissue. Similarly, when the tissue shaver 40 (FIGS. 2A-2B) is placed tangentially against the targeted tissue, the rotating and linearly moving inner cutting member 250 shears the tissue to be cut.

Referring back to FIGS. 4C and 4D, as the helical drive member 130 and the inner drive hub 110 (FIGS. 2A-2D) are mechanically driven by the motor of the controller 30, the follower 142 of the coupling piece 140 follows the helical channels 136 and 138, swiveling, while the follower 142 smoothly transitions from the first helical channel 136 to the second helical channel 138 at the ends of the distal portion of the helical drive member 130. The coupling of the follower 142 to the helical channels 136 and 138 causes the helical drive member 130 to also move linearly. Thus, the inner cutting member 150 simultaneously rotates and moves linearly to cut the tissue.

When the helical drive member 130 moves distally, the cutting edge 154 of the inner cutting member 150 advances distally and closes the cutting window 166 (FIGS. 4A and 4B) so that the tissue shaver 40 engages and cuts the tissue, which protrudes into the cutting window 166. Meanwhile, when the helical drive member 130 moves proximally, the cutting edge 154 withdraws proximally and opens the cutting window 166 so that the resulting debris may be aspirated through the cutting window 166 and into the hollow interior 152 of the inner cutting member 150. In addition, the opening of the cutting window 166 allows tissue to be drawn in for the next cut. Because the tissue shaver 40 performs different operations (e.g., cutting, aspirating, etc.) when the helical drive member 130 moves distally or proximally, it may be advantageous to optimize the movement of the helical drive member 130 according to the different functions. For example, in some cases, it may be advantageous to retract the helical drive member 130 more slowly in the proximal direction and thus keep the cutting window 166 open for a relatively longer period of time after a cut to allow sufficient aspiration of debris and to provide time for more tissue to enter the cutting window 166 in preparation for the next cut. Accordingly, aspects of the present disclosure provide a helical drive member 130 that is configured to move linearly at different rates depending on its position and/or direction of movement.

In an aspect, the helical drive member 130 may follow a predetermined angular position, velocity, and/or acceleration profile to prevent overshoots and to make smooth transitions when the inner cutting member 150 reaches the proximal-most or distal-most end of its travel path. Further, the predetermined angular position, velocity, and/or acceleration profile may be provided independent of or in conjunction with a feedback system.

The legs 142b of the follower 142 of the coupling piece 140 travel over the helical channels 136 and 138 to produce the desired linear motion of the helical drive member 130 from the input rotary motion. Movement of the coupling piece 140 along the first helical channel 136 causes the helical drive member 130 to move distally and causes the cutting device to perform the cutting operation. Meanwhile, movement of the coupling piece 140 along the second helical channel 138 causes the helical drive member 130 to move proximally and allows the cutting device to perform the aspirating operation and draw more tissue into the cutting window 166 for cutting.

The first helical channel 136 is defined by a thread with a first helical angle or pitch. As shown in FIGS. 3A-3B, the thread for the first helical channel 136 defines four turns 137a-d distributed evenly along a distance of the helical drive member 130. Meanwhile, the second helical channel 138 is defined by a thread with a second helical angle or pitch. The thread for the second helical channel 138 defines six turns 139a-f distributed evenly along the same distance of the helical drive member 130. Thus, the first helical channel 136 has fewer turns than the second helical channel 138 over the same distance. The number of turns over a distance generally corresponds to the number of rotations required by the helical drive member 130 to travel linearly over the same distance. To define more turns over a given distance of the helical drive member 130, a thread must generally have a smaller helical angle or pitch. Thus, the second helical angle or pitch associated with the second helical channel 138 is smaller than the first helical angle or pitch associated with the first helical channel 136.

To move linearly over a given distance, the helical drive member 130 must make fewer rotations when the coupling piece 140 travels over the first helical channel 136, e.g., when the helical drive member 130 moves distally. Conversely, the helical drive member 130 must make more rotations when the coupling piece 140 travels over the second helical channel 138, e.g., when the helical drive member 130 moves proximally. When the helical drive member 130 is rotated at a constant speed, (1) the helical drive member 130 moves at a relatively faster linear speed when it is moving distally to perform the cutting operation and (2) conversely, the helical drive member 130 moves at a relatively slower linear speed when the helical drive member 130 is moving proximally to perform the aspirating operation and draw more tissue into the cutting window 166 for subsequent cutting.

The first helical channel 136 may be configured with a particular helical angle or pitch so that the inner cutting member 150 performs the cutting operation at a particular linear speed for optimal performance Meanwhile, the second helical channel 138 may be configured with a relatively smaller helical angle or pitch to keep the cutting window 166 at least partially open for a longer time. As described above, it may be advantageous to move the helical drive member 130 more slowly in the proximal direction and thus keep the cutting window 166 open for a longer period of time after a cut. This allows for sufficient aspiration of debris and provides time for more tissue to enter the cutting window 166 in preparation for the next cut.

Although the thread for the first helical channel 136 defines four turns 137a-d and the thread for the second helical channel 138 defines six turns 139a-f over the same linear distance of the helical drive member 130, it is understood that, in other embodiments, the first helical channel 136 and the second helical channel 138 may be configured with different respective helical angles so they have different respective numbers of turns than shown in FIGS. 3A-3C. In addition, although the entire length of the first helical channel 136 may be defined by the first helical angle or pitch and the entire length of the second helical channel 138 may be defined by the second helical angle or pitch in FIGS. 3A-3C, it is understood that other implementations may employ one or more helical channels that are defined by multiple helical angles or pitches that cause the helical member to move at various different speeds as the helical member moves in one direction. Furthermore, it is understood that in alternative implementations, the helical channels may be configured so that the first helical channel has a smaller helical angle than the helical angle of the second helical channel, thereby causing the helical member to move relatively slower toward the distal end (to perform the cutting operation more slowly) and relatively faster away from the distal end (to perform the aspirating operation, etc. more quickly).

The helical drive member 130 is detailed above for use in the tissue shaver 40. It is understood, however, that aspects of the helical drive member 130 may be employed in other types of cutting devices or rotation and/or translation type surgical devices to achieve corresponding advantages.

In general, according to some aspects of the present disclosure, such as those detailed above, tissue shavers employ a helical member with helical channels that are configured to provide optimal linear motion. The helical channels may be smoothly blended at their ends to provide a continuous channel that provides for a change in direction at the ends of the linear motion. In particular, the helical channels are defined by threads with different helical angles so that the rotation of the helical member causes linear movement at different desired linear speeds.

The resulting linear movement may involve relative movement between any components of the tissue shavers (or other surgical instruments) and are not limited to the examples and implementations described herein. For example, the helical member may be fixed to a first component (e.g., in a housing) such that rotation of the helical member relative to a second component also causes relative linear movement between the first and second components. In accordance with some implementations of the present disclosure, the helical member may be stationary and a follower may be permitted to move linearly along the helical member, such as in a carriage or guide. The follower may be coupled to the inner member to cause the inner member to move linearly as the follower is moved by rotational motion of the helical member. A separate drive train, such as gears, belts and pulleys, may be used to impart rotary motions on the inner member. In accordance with some implementations of the present disclosure, the inner member may rotate about the same axis, a parallel axis, or a non-parallel axis as the helical member.

Figure 9A:
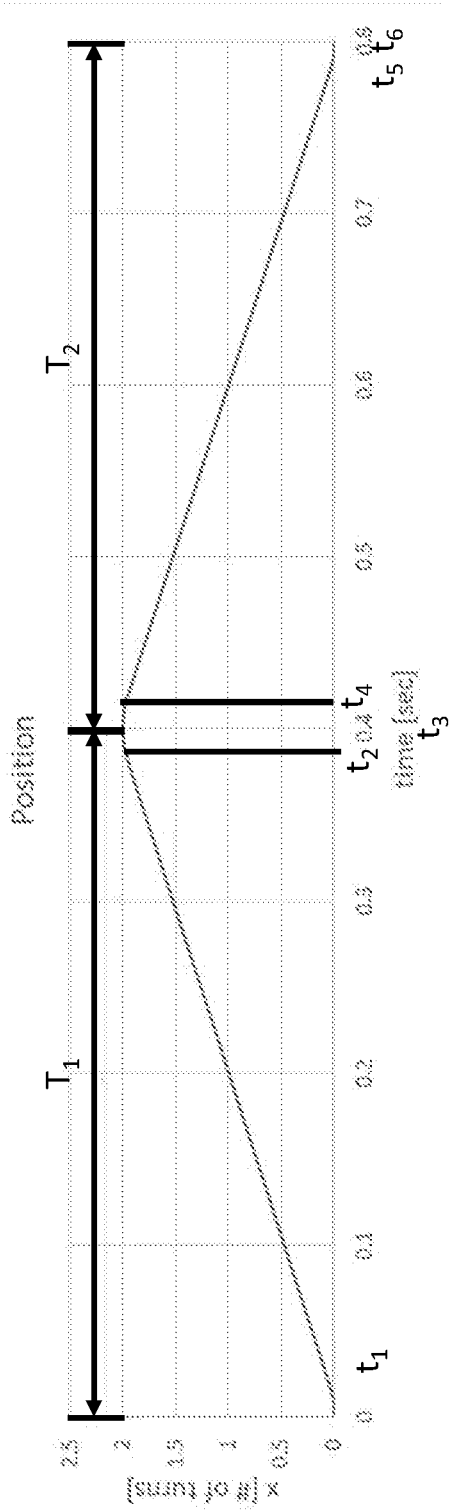
FIGS. 9A-9D illustrate piecewise continuous profiles for angular position, velocity, acceleration, and jerk for a tissue shaver according to aspects of the present disclosure.
Figure 9B:
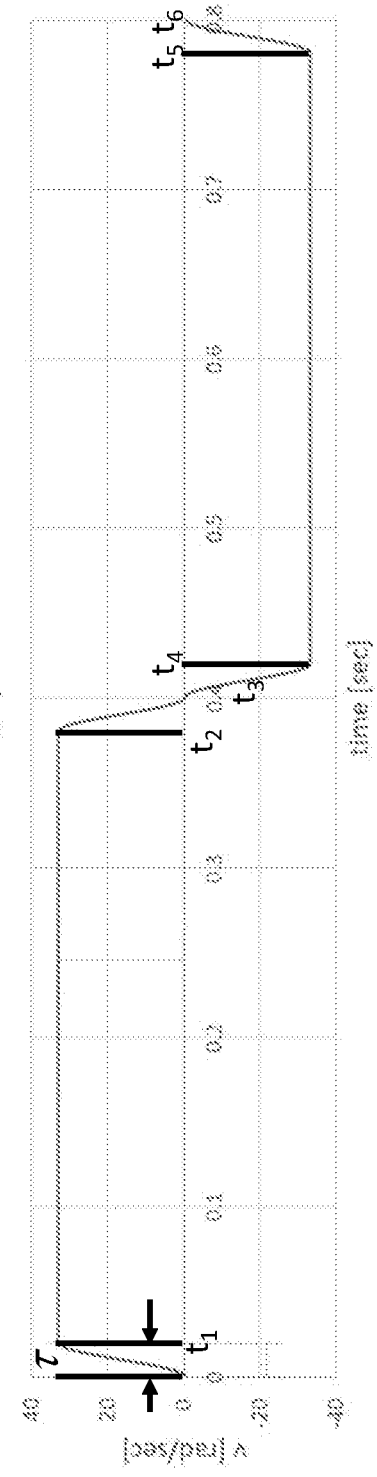
Figure 9C:
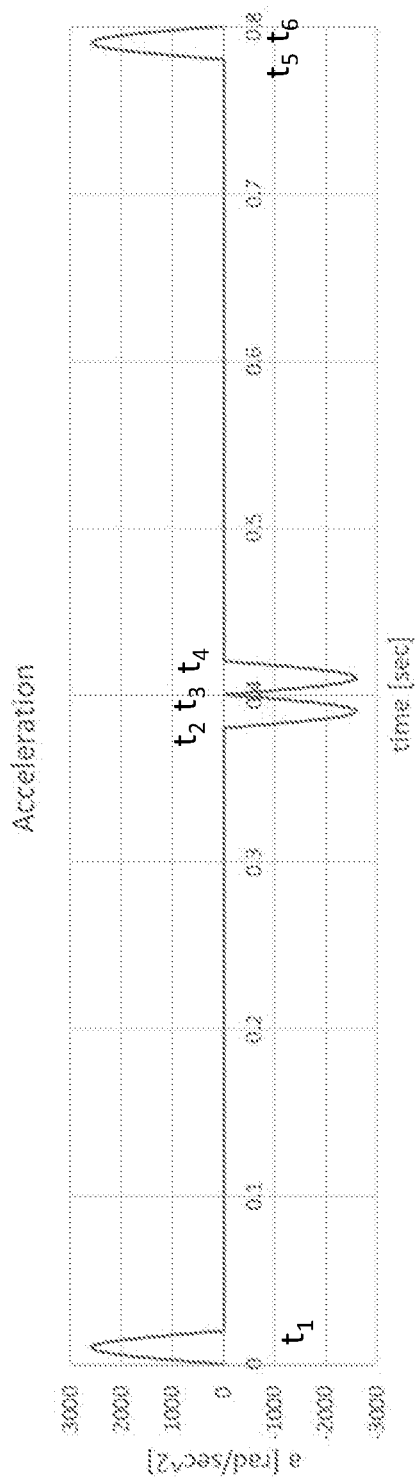
Figure 9D:
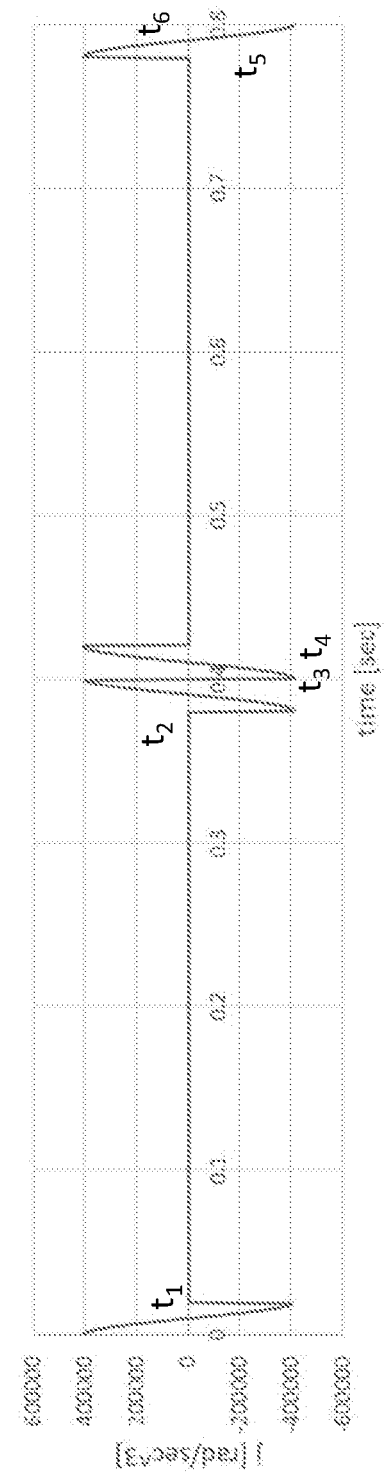

FIGS. 9A-9D illustrate piecewise continuous profiles for a rotating and reciprocating drive component, e.g., a helical drive member of a tissue shaver, according to embodiments of the present disclosure. In particular, FIG. 9A shows piecewise continuous profiles for angular positions of the drive component for a period; FIG. 9B shows piecewise continuous profiles for angular velocities of the drive component for the period; FIG. 9C shows piecewise continuous profiles for angular accelerations of the drive component for the period; and FIG. 9D shows piecewise profiles for angular jerks of the drive component for the period. The angular velocity is a first derivate of the angular position, the angular acceleration is a second derivate of the angular position, and the angular jerk is a third derivative of the angular position.

The piecewise continuous profiles shown in FIGS. 9A-9D are provided as references in controlling the drive component. That is, when controlling the angular position of the drive component, the curve shown in FIG. 9A provides the reference angular positions. In other words, the current angular position of the drive component is compared with the angular position of the curve. When the current angular position is behind the reference angular position of the curve of FIG. 9A, for example, the controller causes more power to be supplied to the motor thereof or otherwise directs the motor so that the drive component moves faster to catch the reference angular position. When the current angular position is ahead of the reference angular position, as another example, the controller causes less power to be supplied to the motor thereof or otherwise directs the motor so that the drive component moves slower to follow the reference angular position. In an aspect, the controller may adjust the power supplied based on one or more of the reference angular position, velocity, acceleration, and jerk of FIGS. 9A-9D.

The piecewise continuous profiles may have zero initial and final values during the period. For example, as shown in FIGS. 9A and 9B, the initial angular position at zero seconds and the final position at 0.8 seconds are zero, and the initial angular velocity at zero seconds and the final angular velocity at 0.8 seconds are also zero, when the period is 0.8 seconds. Thus, advancing the drive component from a proximal-most position to a distal-most position and retracting from the distal-most position to the proximal-most position can be made smooth, and transient current spikes can be minimized in driving the drive component.

The period may include six sub periods: the first sub period $[0, t_1]$ is from 0 to $t_1$ or 0.01 seconds, the second sub period $[t_1, t_2]$ is from $t_1$ to $t_2$ or from 0.01 to 0.399 seconds, the third sub period $[t_2, t_3]$ is from $t_2$ to $t_3$ or from 0.399 to 0.4 seconds, the fourth sub period $[t_3, t_4]$ is from $t_3$ to $t_4$ or from 0.4 to 0.401 seconds, the fifth sub period $[t_4, t_5]$ is from $t_4$ to $t_5$, or from 0.401 to 0.799 seconds, and the sixth sub period $[t_5, t_6]$ is from $t_5$ to $t_6$ or from 0.799 to 0.8 seconds. As such, the piecewise continuous profiles for the angular position, the angular velocity, the angular acceleration, and the angular jerk for the six sub periods are shown in FIG. 9A-9D, respectively. Further, the period may include first and second half periods. The first half period $T_1$ from the first sub period to the third sub period may be a duration while the drive component advances from the proximal-most position to the distal-most position thereof, and the second half period $T_2$ from the fourth sub period to the sixth sub period is a duration while the drive component retracts from the distal-most position to the proximal-most position thereof. Even though both half periods $T_1$ and $T_2$ are shown being equal, the first half period $T_1$ may be shorter or longer than the second half period $T_2$. By lengthening or shortening one of the half periods, it is possible to make the retracting time slower than the advancing time so as, for example with respect to a tissue shaver, to aspirate cut tissue or to make the advancing time slower than the retracting time so as to properly cut tissue.

The first sub period $[0, t_1]$ is for the advancing velocity of the drive component to be increased from zero to a top velocity plateau, or the maximum speed as shown in FIG. 9B. Thus, the first sub period $[0, t_1]$ may be called as a rise time τ. During the first sub period, the angular position of the drive component is increased slowly as shown in FIG. 9A. The rise time τ is critical because if the rise time τ is too short, an overshoot may occur and if the rise time τ is too long, it would take too much time and/or be more difficult to cut tissue. In this regard, the rise time τ may be set to be less than or equal to one fortieth of the first half period $T_1$.

As shown in FIG. 9B, the second sub period $[t_1, t_2]$ is when the top velocity plateau of the drive component is maintained. During the second sub period $[t_1, t_2]$, the drive component linearly advances to the distal end thereof as shown in FIG. 9A.

The third and fourth sub periods $[t_2, 0]$ and $[t_3, t_4]$ may be a transition period, during which the drive component changes its moving direction from forward to backward. During the third sub period $[t_2, t_3]$, the drive component reduces its advancing velocity as the drive component is approaching the distal-most position thereof. At the end of the third sub period $[t_2, t_3]$ or simply at $t_3$, the drive component reaches the distal-most position, and the advancing velocity becomes zero, as shown in FIG. 9B. The angular position of the drive component also reaches the two full turns at $T_1$, as shown in FIG. 9A. Thus, the third sub period $[t_2, t_3]$ may be called as a fall time, which may be different from or equal to the rise time τ. With respect to the helical drive member 130 (FIGS. 3A-3C) as the drive component, for example, the inner cutting member 150 (FIGS. 2A and 23B) changes its moving direction from the distal-most position towards the proximal-most position after $t_3$.

In FIG. 9A, the distance that the drive component advances is shown as a number of turns. For example, at time $t_3$, the number of turns is two, when the drive component reaches the distal-most position. In an aspect, the number of turns may be four. For example, with respect to the helical drive member 130, the first helical channel 136 as shown in FIGS. 3A and 3B is right-hand threaded used for advancing the drive component and includes four turns. Thus, the number of turns shown in FIG. 9A may be dependent upon the number of turns of the first helical channel of the drive component for advancing to the distal-most position.

The number of turns shown in FIG. 9A may not be equal to a distance from the proximal-most position to the distal-most position. Rather, the number of turns may indicate an angular position. For example, one full turn is 2π radian and a quarter turn is π/2 radian. In reality, the angular position may be identified as an incremental encoder count. When there are 100 encoder counts in a full turn, 50 encoder count means a half turn or π radian. Thus, based on the number of encoder counts in a full turn, the angular position of the drive component may be determined, and likewise a distance that the drive component advances from the proximal-most position or retracts from the distal-most position may be determined based on the length of the drive component.

In another aspect, the angular position of the drive component may be measured by an encoder counter or a hall sensor-based position measurement device. This list of devices which can measure the angular position is provided as an example and may include other measurement devices, which are readily available to a person having ordinary skill in the art.

The fall time in the second half period $T_2$ is the fourth sub period $[t_3, t_4]$. The fall time may be equal to the rise time $\tau$. During the fourth sub period $[t_3, t_4]$, the drive component starts retracting from the distal-most position towards the proximal-most position as shown in FIG. 9A. At the end of the fourth sub period $[t_3, t_4]$ or at $t_4$, the angular velocity of the drive component reaches a bottom velocity plateau, or the minimum velocity or the maximum speed as shown in FIG. 9B.

During the fifth sub period $[t_4, t_5]$, the drive component maintains the constant velocity as shown in FIG. 9B, and the drive component linearly retracts from the distal-most position as shown in FIG. 9A. The fifth sub period $[t_4, t_5]$ may be equal to the second sub period $[t_1, t_2]$. Further, the absolute value of the bottom velocity plateau may be equal to the absolute value of the top velocity plateau, meaning that the retracting speed may be equal to the advancing speed. With this scenario, for example with respect to helical drive member 130 as the drive component, a number of turns of the first helical channel 136 of FIGS. 3A and 3B may be equal to a number of turns of the second helical channel 138.

In an aspect, as described above with respect to FIGS. 3A and 3B, the second helical channel 138 may have six turns while the first helical channel 136 may have four turns. In this scenario, when the angular velocity for advancing the drive component may be equal to the angular velocity for retracting the drive component, the fifth sub period $[t_4, t_5]$ is longer than the second sub period $[t_1, t_2]$ so that the drive component may make the six turns with the same speed and thus move back from the distal-most position slower than advancing to the distal-most position.

In another aspect, the absolute value of the bottom velocity plateau may be larger than the absolute value of the top velocity plateau. In this scenario, the fifth sub period $[t_4, t_5]$ may be equal to the second sub period $[t_1, t_2]$ when the second helical member 138 has six turns while the first helical member 136 has four turns. In this way, the number of turns of the first and second helical channels 136 and 138 may be adjusted or the retracting or advancing velocity may be adjusted to appropriately cut the tissue and to aspirate cut tissue. In still another aspect, both of the number of turns and the retracting or advancing velocity may be simultaneously adjusted.

During the sixth sub period $[t_5, t_6]$, the retracting velocity is increased from the bottom velocity plateau to zero as shown in FIG. 9B. In other words, the retracting speed is decreased from the maximum speed to zero. During the sixth sub period, the angular position of the drive component slowly reaches the zero position, meaning that the drive component reaches the proximal-most position. In an aspect, the sixth sub period $[t_5, t_6]$ may be longer than or equal to the rise time $\tau$ of the first sub period $[0, t_1]$.

As described above, each of the curves for the angular position and the angular velocity includes six piecewise continuous profiles and the combination of the six piecewise profiles is also continuous, as shown in FIGS. 9A and 9B. Continuous properties of these piecewise profiles may provide reference angular positions and angular velocities for the drive component to control movements of the drive component without abrupt movements.

FIG. 9C shows a curve for angular accelerations of the drive component. The curve also includes six piecewise continuous profiles and is continuous during the full period. To prevent an overshoot, the acceleration is increased gradually during the first half of the first and sixth sub periods and during the second half of the third and fourth sub periods, and decreased to zero during the first half of the third and fourth sub periods and during the second half of the first and sixth sub periods. In contrast, during the second and fifth sub periods, the angular acceleration of the drive component is maintained to be zero, meaning that no additional energy may be supplied to the drive component.

Since the second and fifth sub periods occupy most of the full period and the other sub periods occupy only small portions, constant amount of power may be supplied to the motor to cause the drive component to advance to or retract from the distal-most position of the drive component for most of the full period, and for only small portions of the full period, additional power may be supplied to the motor to drive the drive component, so that control of the movements of the drive component becomes easily implemented.

Further, when similar shapes for the angular acceleration of the drive component are utilized during the first, third, fourth, and sixth sub periods, the control of the movements of the drive component becomes much easier by employing similar controls for those sub periods than utilizing different shapes each for those sub periods.

Provided in FIG. 9D is a curve for jerks of the drive component. The curve also includes six piecewise continuous profiles. Unlike the angular position, velocity, and acceleration, the angular jerks of the drive component are not continuous at $t_1$, $t_2$, $t_3$, $t_4$, $t_5$, and $t_6$. By controlling the angular jerk, the movement of the drive component may be prevented from abrupt movements while advancing to and retracting from the distal-most position of the drive component.

In an aspect, the movements of the drive component may be controlled by one or more of the angular position, the angular velocity, the angular acceleration, and the angular jerk as shown in FIGS. 9A-9D.

Below is one example of six piecewise continuous profiles for the angular position, angular velocity, angular acceleration, and angular jerk as shown in FIGS. 9A-9D. A combination of the six piecewise continuous profiles for each of the angular position, angular velocity, and angular acceleration also shows continuity during the full period. Following equations define the six sub periods:

the first sub period: $0 \leq t_1 < \tau$;

the second sub period: $\tau \leq t_2 < T-\tau$;

the third sub period: $T-\tau \leq t_3 < T$;

the fourth sub period: $T \leq t_4 < T+\tau$;

the fifth sub period: $T+\tau \leq t_5 < 2T-\tau$; and the sixth sub period: $2T-\tau \leq t_6 < 2T$, where T is a half period, 2T is the full period, and $\tau$ is a rise time that the drive component can reach from zero to the top velocity plateau. To differentiate each piecewise profile from the others, a separate parameter is used for each sub period: $t_1$ for the first sub period, $t_2$ for the second sub period, $t_3$ for the third sub period, $t_4$ for the fourth sub period, $t_5$ for the fifth sub period, and $t_6$ for the sixth sub period. As described above, the rise time $\tau$ may be less than or equal to one fortieth of the half period T. In an aspect, the relationship between the rise time $\tau$ and the half period T may be adjusted based on requirements of the drive component or surgical instrument, e.g., tissue shaver.

The following equations are examples for the angular position $x(t_1)$, the angular velocity $v(t_1)$, the angular acceleration $a(t_1)$, and the angular jerk $j(t_1)$ for the first sub period:

$$x(t_1) = \frac{V_0}{2}\left(t_1 - \frac{\tau}{\pi}\sin\frac{\pi}{\tau}t_1\right);$$

$$v(t_1) = \frac{V_0}{2}\left(1 - \cos\frac{\pi}{\tau}t_1\right);$$

$$a(t_1) = \frac{\pi V_0}{2\tau}\sin\frac{\pi}{\tau}t_1; \text{ and}$$

$$j(t_1) = \frac{\pi^2 V_0}{2\tau^2}\cos\frac{\pi}{\tau}t_1.$$

The initial values for the angular position, velocity, and acceleration are all zeros when $t_1$ is equal to zero as shown in FIGS. 9A-9D. Further, the following derivative relationships among the angular position, angular velocity, angular acceleration, and angular jerk are satisfied:

$$v(t_1) = \frac{d}{dt_1}x(t_1);$$

$$a(t_1) = \frac{d}{dt_1}v(t_1) = \frac{d^2}{d^2t_1}x(t_1); \text{ and}$$

$$j(t_1) = \frac{d}{dt_1}a(t_1) = \frac{d^2}{d^2t_1}v(t_1) = \frac{d^3}{d^3t_1}x(t_1).$$

The following equations are examples for the angular position $x(t_2)$, the angular velocity $v(t_2)$, the angular acceleration $a(t_2)$, and the angular jerk $j(t_2)$ for the second sub period:

$$x(t_2) = V_0\left(t_2 - \frac{\tau}{2}\right);$$

$$v(t_2) = V_0;$$

$$a(t_1) = 0; \text{ and}$$

$$j(t_1) = 0.$$

When the time is at the boundary between the first and second sub periods, namely that $t_1$ and $t_2$ are $\tau$, the following relationships stand:

$$x(t_1) = x(t_2) = \frac{V_0\tau}{2},\ v(t_1) = v(t_2) = V_0,$$

and $a(t_1)=a(t_2)=0$. That means two consecutive piecewise profiles of the angular position $x(t)$, the angular velocity $v(t)$, and the angular acceleration $a(t)$ are continuous at $\tau$. As shown above, the following derivative relationships among the angular position, angular velocity, angular acceleration, and angular jerk are satisfied:

$$v(t_2) = \frac{d}{dt_2}x(t_2);$$

$$a(t_2) = \frac{d}{dt_2}v(t_2) = \frac{d^2}{d^2t_2}x(t_2); \text{ and}$$

$$j(t_2) = \frac{d}{dt_2}a(t_2) = \frac{d^2}{d^2t_2}v(t_2) = \frac{d^3}{d^3t_2}x(t_2).$$

Since the above derivative relationships among the angular position, angular velocity, angular acceleration, and angular jerk for the other sub periods are also satisfied in the same way, the derivative relations for the other sub periods are not described below.

Further, the angular position of the drive component for the first sub period is a combination of a linear function and a trigonometric function, and the angular position of the drive component for the second sub period is another linear function. Each of the linear functions and the trigonometric function is continuous. Since both piecewise functions for the first and second sub periods are continuous at $\tau$, the combination of the two piecewise continuous profiles are also continuous over the first and second sub periods. In an aspect, the trigonometric function may be replaced with any other continuous function which prevents overshoots and provides initial smooth motions for the drive component for the first sub period. Such a continuous function may be, for example, polynomial functions with a power greater than or equal to three, logarithmic functions, exponential functions, trigonometric functions or any combination thereof.

The linear function for the first sub period may have the same slope as the slope of the linear function for the second sub period, even though the linear function for the first sub period is different from the linear function for the second sub period.

The following equations are examples for the angular position $x(t_3)$, the angular velocity $v(t_3)$, the angular acceleration $a(t_3)$, and the angular jerk $j(t_3)$ for the third sub period:

$$x(t_3) = \frac{V_0}{2}\left(t_3 + T - 2\tau - \frac{\tau}{\pi}\sin\frac{\pi}{\tau}(t_3 - T)\right);$$

$$v(t_3) = \frac{V_0}{2}\left(1 - \cos\frac{\pi}{\tau}(t_3 - T)\right);$$

$$a(t_3) = \frac{\pi V_0}{2\tau}\sin\frac{\pi}{\tau}(t_3 - T); \text{ and}$$

$$j(t_3) = \frac{\pi^2 V_0}{2\tau^2}\cos\frac{\pi}{\tau}(t_3 - T).$$

When the time is at the boundary between the second and third sub periods, namely that $t_2$ and $t_3$ are $T-\tau$, the following relationships stand:

$$x(t_2) = x(t_3) = V_0\left(T - \frac{3\tau}{2}\right),\ v(t_2) = v(t_3) = V_0,$$

and $a(t_2)=a(t_3)=0$. That means two consecutive piecewise profiles for the angular position, the angular velocity, and the angular acceleration for the second and third sub periods are continuous at $T-\tau$.

The following equations are examples for the position $x(t_4)$, the speed $v(t_4)$, acceleration $a(t_4)$, and the jerk $j(t_4)$ for the fourth sub period:

$$x(t_4) = -\frac{V_0}{2}\left(t_4 - 3T + 2\tau - \frac{\tau}{\pi}\sin\frac{\pi}{\tau}(t_4 - T)\right);$$

-continued $$v(t_4) = -\frac{V_0}{2}\left(1 - \cos\frac{\pi}{\tau}(t_4 - T)\right);$$

$$a(t_4) = -\frac{\pi V_0}{2\tau}\sin\frac{\pi}{\tau}(t_4 - T); \text{ and}$$

$$j(t_4) = -\frac{\pi^2 V_0}{2\tau^2}\cos\frac{\pi}{\tau}(t_4 - T).$$

When the time is at the boundary between the third and fourth sub periods, namely that $t_3$ and $t_4$ are T, the following relationships stand: $x(t_3)=x(t_4)=V_0(T-\tau)$, $v(t_3)=v(t_4)=0$, and $a(t_3)=a(t_4)=0$. That means two consecutive piecewise profiles for the angular position, the angular velocity, and the angular acceleration for the third and fourth sub periods are continuous at T.

Furthermore, each of the piecewise continuous functions for the third and fourth sub periods includes one linear function and a trigonometric function. Both slopes of the linear functions have the same value but have different signs. As shown in FIGS. 9A and 9B, the piecewise continuous profile for the third sub period has a mirror image around $t_3$ as the piecewise continuous profile for the fourth sub period.

The following equations are examples for the angular position $x(t_5)$, the angular velocity $v(t_5)$, the angular acceleration $a(t_5)$, and the angular jerk $j(t_5)$ for the fifth sub period:

$$x(t_5) = -\frac{V_0}{2}(2t_5 - 4T + \tau);$$

$$v(t_5) = -V_0;$$

$$a(t_5) = 0; \text{ and}$$

$$j(t_5) = 0.$$

When the time is at the boundary between the fourth and fifth sub periods, namely that $t_4$ and $t_5$ are T+τ, the following relationships stand:

$$x(t_4) = x(t_5) = V_0\left(T - \frac{3\tau}{2}\right), v(t_4) = v(t_5) = -V_0,$$

and $a(t_4)=a(t_5)=0$. That means two consecutive piecewise profiles for the angular position, the angular velocity, and the angular acceleration for the fourth and fifth sub periods are continuous at T+τ.

During the fifth sub period, the angular position of the drive component linearly retracts from the distal-most position as shown in FIG. 9A and the angular velocity is maintained constant at the bottom velocity plateau as shown in FIG. 9B. As described with respect to the first and second sub periods, the angular position of the drive component for the fourth sub period is a combination of a linear function and a trigonometric function, and the angular position of the drive component for the fifth sub period is another linear function. The slope of the linear profile for the fourth sub period is equal to the slope of the linear profile for the fifth sub period. In an aspect, the trigonometric function may be replaced with any other continuous function which prevents overshoots and provides initial smooth motions for the drive component for the fourth sub period. Such a continuous function may be, for example, polynomial functions with a power greater than or equal to three, logarithmic functions, exponential functions, trigonometric functions or any combination thereof.

The following equations are examples for the angular position $x(t_6)$, the angular velocity $v(t_6)$, the angular acceleration $a(t_6)$, and the angular jerk $j(t_6)$ for the sixth sub period:

$$x(t_6) = \frac{V_0}{2}\left(t_6 + T - 2\tau - \frac{\tau}{\pi}\sin\frac{\pi}{\tau}(t_6 - 2T)\right);$$

$$v(t_6) = -\frac{V_0}{2}\left(1 - \cos\frac{\pi}{\tau}(t_6 - 2T)\right);$$

$$a(t_6) = -\frac{\pi V_0}{2\tau}\sin\frac{\pi}{\tau}(t_6 - 2T); \text{ and}$$

$$j(t_6) = -\frac{\pi^2 V_0}{2\tau^2}\cos\frac{\pi}{\tau}(t_6 - 2T).$$

When the time is at the boundary between the fifth and sixth sub periods, namely that $t_5$ and $t_6$ are 2T−τ, the following relationships stand:

$$x(t_5) = x(t_6) = \frac{V_0 \tau}{2}, v(t_5) = v(t_6) = -V_0,$$

and $a(t_5)=a(t_6)=0$. That means two consecutive piecewise profiles for the angular position, the angular velocity, and the angular acceleration for the fifth and sixth sub periods are continuous at 2T−τ.

Further, the final values for the angular position, the angular velocity, and the angular acceleration of the drive component at the end of the period are all zeros. Thus, in the next period, the two consecutive piecewise functions during the sixth sub period and the next first sub period are continuous at the start of the next period. Consequently, the six piecewise curves, each of which is continuous, are all continuous during the full period and throughout all time.

FIGS. 9A-9D show curves of the examples of the angular positions, the angular velocities, the angular accelerations, and the angular jerks for the drive component according to the above equations for the six sub periods, when the half period T is equal to 0.4 second and the rise time τ is equal to 0.01 second, which is equal to one fortieth of T, and $V_0$ is equal to $$\frac{4\pi}{(T - \tau)}$$

or about 0.32.22 radian. In other words, the curves are based on the following equations and the above equations for the angular position, velocity, acceleration, and jerk:

$$T = 0.4;$$

$$\tau = T/40;$$

$$V_{rpm} = \frac{120}{(T - \tau)}; \text{ and}$$

$$V_0 = \frac{V_{rpm}\pi}{30},$$

where T is one half of the period, τ is the rise time, $V_{rmp}$ is the velocity plateau in revolution per minute and is about 307 revolutions per minute, and $V_0$ is the angular velocity per second in radian. Based on these relationships, when the half period or the period is determined, the rise time, and the velocity plateau (the maximum velocity) can be automatically determined. Likewise, when $V_{rmp}$ is determined, the velocity plateau, the half period, and the rise time can be automatically determined. Accordingly, determination of only one parameter can generate reference angular positions, velocities, accelerations, and jerks for the drive component during the period.

In an aspect, two parameters can be input to the system when the half period T and the rise time τ are independent. In this case, the half period and the rise time are input. Or the velocity plateau $V_{rpm}$ and the rise time τ may be input. In another aspect, any number of parameters can be input when each of the input parameters is to be independently controlled.

Figure 10:
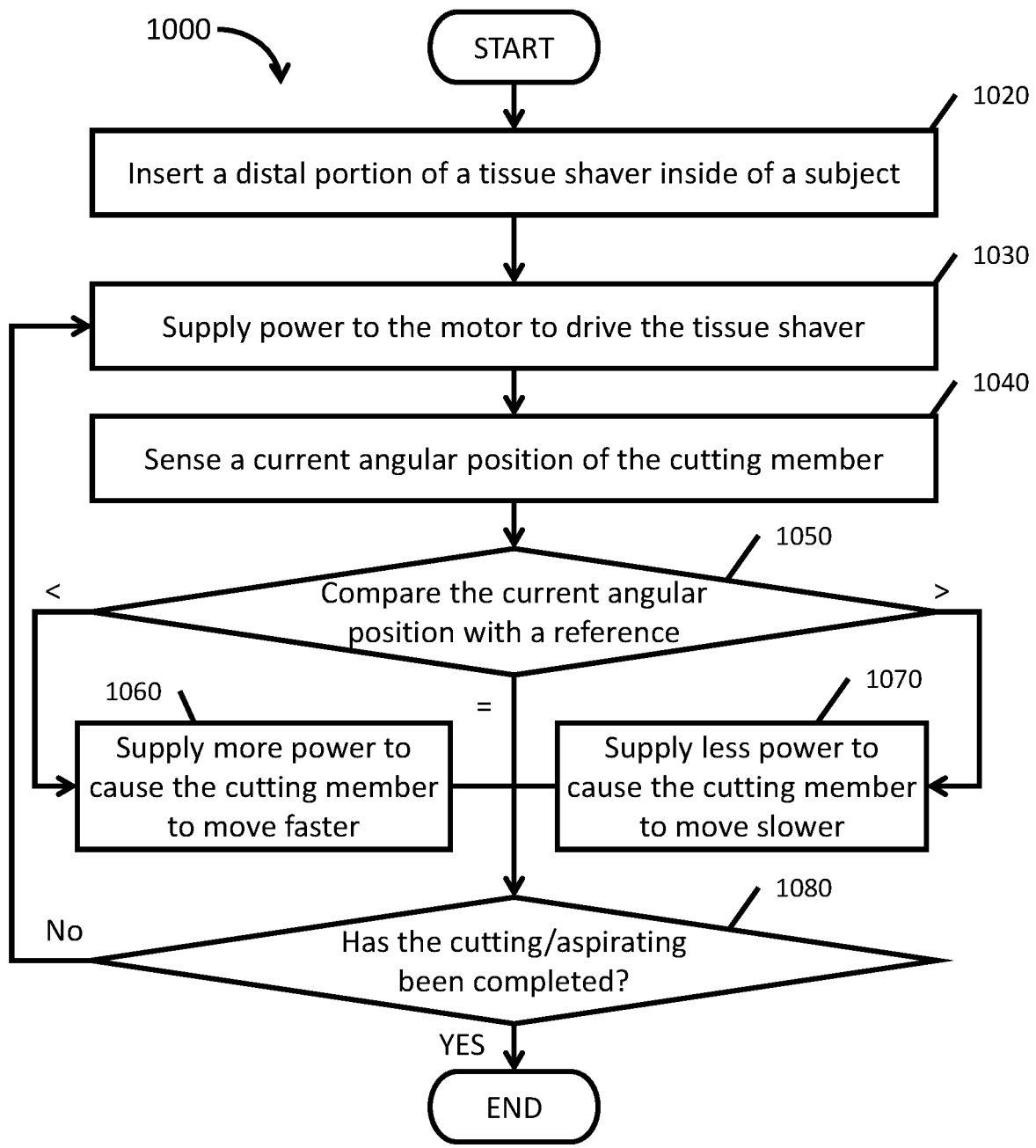
FIG. 10 illustrates a flowchart for controlling a tissue shaver based on a reference according to aspects of the present disclosure.

FIG. 10 is a flowchart showing a method 100 for controlling a drive component of a tissue shaver such that use of the tissue shaver is controlled based on a reference profile according to embodiments of the present disclosure. The method 1000 starts by inserting a distal portion of the tissue shaver inside of a patient in step 1020 to a position adjacent tissue of interest to be cut and removed. The tissue shaver may be inserted through a working channel, which navigates through a luminal network of the patient or an orifice of the patient. The tissue shaver may include a cutting member in the form of an inner cutting member disposed within an outer member defining a cutting window as shown in FIGS. 5A and 5B, through which a target tissue can be cut and aspirated. Other configurations are also contemplated.

Power is then supplied to the motor to drive tissue shaver in step 1030 to activate the cutting member to rotate and move forward and backwards so as to cut and aspirate tissue drawn into the cutting window. This movement of the cutting member is caused by rotational driving, by the motor, of the helical drive member 130 of the tissue shaver as shown in FIGS. 4A-4D. Thus, the position of the cutting member is measured by an angular position of the cutting member directly or indirectly via an angular position of a component fixed to the cutting member such as the drive component, e.g., helical drive member 130.

In step 1040, the current angular position is sensed by an encoder counter or a hall sensor-based position measurement device and received. In an aspect, instead of the angular position, an angular velocity, acceleration, or jerk may be sensed and received.

The current angular position may be compared with a reference angular position in step 1050. In this step, the current angular velocity, acceleration, or jerk may be compared with a reference angular velocity, acceleration, or jerk. Each of the reference angular position, velocity, acceleration, or jerk may include six piecewise continuous profiles for corresponding six sub periods as shown in FIGS. 9A-9D. In an aspect, one of the current angular velocity, acceleration, and jerk may be compared with the corresponding reference in step 1050. In another aspect, more than one of the current angular velocity, acceleration, and jerk may be compared to increase controllability over the tissue shaver.

When it is determined in step 1050 that the current angular position is less than the reference angular position, more power is supplied to the motor to drive the cutting member to increase its angular velocity to catch the reference angular position in step 1060. When it is determined in step 1050 that the current angular position is greater than the reference angular position, less power is supplied to the motor to decrease the angular velocity of the cutting member to follow the reference angular position in step 1070.

When it is determined in step 1050 that the current angular position is equal to the reference angular position or after steps 1060 and 1070, the method 1000 moves to step 1080, in which it is determined whether or not the cutting and aspirating has been completed. When it is determined that the cutting and aspirating has not been completed, steps 1030-1080 are repeated until completion.

After completion of the cutting and aspirating, the method 1000 is ended. The same operations may be initiated for cutting and aspirating another target tissue after completion of the method 1000.

Based on the piecewise continuous profiles, the controller may control the tissue shaver in a desired way to appropriately cut tissue and aspirate the cut tissue.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical instrument configured to cut tissue, comprising:
    an outer member and an inner member at least partially received within the outer member, the outer member including a cutting window near a distal end of the outer member;
    a drive hub mechanically coupled to the inner member and configured to drive the inner member to rotate around and move along a longitudinal axis of the outer member; and
    a controller configured to control the drive hub to control at least one of an angular position, an angular velocity, or an angular acceleration of the inner member according to a plurality of piecewise continuous profiles such that the inner member is rotated and moved along the longitudinal axis of the outer member for a predetermined period from a proximal-most position to a distal-most position to cut tissue extending into the cutting window, wherein initial and final angular velocities of the inner member for the predetermined period are zero, wherein a first profile among the plurality of piecewise continuous profiles includes a continuous function for the angular position, the angular velocity, or the angular acceleration for the inner member during a rise time of the predetermined period, wherein a second profile among the plurality of piecewise continuous profiles, which follows the first profile, includes a constant velocity and zero acceleration of the inner member during a time, which is after the rise time, of the predetermined period, wherein the first and second profiles are different from each other, wherein a final velocity of the inner member at an end of the rise time is equal to the constant velocity, and wherein a linear relationship between the rise time and the predetermined period is predetermined.

2. The surgical instrument according to claim 1, wherein a forward velocity of the inner member is higher than a backward velocity of the inner member.

3. The surgical instrument according to claim 1, wherein a period during which the inner member moves from the distal-most position to the proximal-most position is equal to the predetermined period.

4. The surgical instrument according to claim 1, wherein the inner member switches a movement direction every predetermined period.

5. The surgical instrument according to claim 1, wherein a third profile among the plurality of piecewise continuous profiles, which follows the second profile, includes a continuous function for the angular position, the angular velocity, or the angular acceleration for the inner member.

6. The surgical instrument according to claim 1, wherein the inner member is fixed to a drive component of the drive hub that includes a first helical groove and a second helical groove thereon along the longitudinal axis.

7. The surgical instrument according to claim 6, wherein the inner member linearly moves along the longitudinal axis based on the first and second helical grooves while the inner member rotates.

8. A surgical instrument configured to cut tissue, comprising:
a cutting member configured to translate along and rotate about a longitudinal axis of the cutting member;
a drive hub coupled to the cutting member and configured to drive the rotation and translation of the cutting member; and
a controller configured to control the drive hub to control at least one of an angular position, an angular velocity, or an angular acceleration of the cutting member according to at least first and second piecewise continuous profiles such that the cutting member is translated along the longitudinal axis for a predetermined period from a proximal-most position to a distal-most position to cut tissue, wherein the first profile includes a continuous function for the angular position, the angular velocity, or the angular acceleration for the cutting member during a rise time of the predetermined period, wherein the second profile is different from the first profile, follows the first profile, and includes a constant velocity of the cutting member during a time of the predetermined period which is after the rise time, wherein a final velocity of the cutting member at an end of the rise time is equal to the constant velocity, and wherein a linear relationship between the rise time and the predetermined period is predetermined.

9. The surgical instrument according to claim 8, wherein a forward velocity of the cutting member is higher than a backward velocity of the cutting member.

10. The surgical instrument according to claim 8, wherein a period during which the cutting member moves from the distal-most position to the proximal-most position is equal to the predetermined period.

11. The surgical instrument according to claim 8, wherein the cutting member switches a movement direction every predetermined period.

12. The surgical instrument according to claim 8, wherein the controller is further configured to control the drive hub to control the at least one of the angular position, the angular velocity, or the angular acceleration of the cutting member according to a third profile that follows the second profile and includes a continuous function for the angular position, the angular velocity, or the angular acceleration for the cutting member.

13. The surgical instrument according to claim 8, wherein the cutting member is coupled to a drive component of the drive hub, the drive component defining at least one helical groove configured to enable the translation of the cutting member in response to rotation of the drive component.

14. The surgical instrument according to claim 8, wherein the cutting member is disposed within an outer member and wherein the rotation and translation of the cutting member is relative to the outer member.

15. The surgical instrument according to claim 8, wherein the controller is configured to control the drive hub by controlling a rotational input to the drive hub.

16. The surgical instrument according to claim 15, wherein the controller is configured to control the rotational input to the drive hub by controlling a motor coupled to the drive hub.

17. The surgical instrument according to claim 16, wherein the cutting member and the drive hub are part of an attachment configured to releasably engage with the motor.

* * * * *